United States Patent
Ito et al.

(10) Patent No.: US 11,249,077 B2
(45) Date of Patent: Feb. 15, 2022

(54) METHOD FOR MAGNETICALLY LABELING PARTICLES AND LABELING APPARATUS

(71) Applicant: ARKRAY, Inc., Kyoto (JP)

(72) Inventors: Hiroshi Ito, Kyoto (JP); Masahiro Kozuka, Kyoto (JP); Takahide Inouchi, Kyoto (JP); Shigeru Kitamura, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 15/720,554

(22) Filed: Sep. 29, 2017

(65) Prior Publication Data

US 2018/0095079 A1    Apr. 5, 2018

(30) Foreign Application Priority Data

Sep. 30, 2016 (JP) ............... JP2016-193792
Sep. 30, 2016 (JP) ............... JP2016-193797
Sep. 28, 2017 (JP) ............... JP2017-188908

(51) Int. Cl.
*G01N 33/543* (2006.01)
*B01D 29/05* (2006.01)
*G01N 33/574* (2006.01)

(52) U.S. Cl.
CPC ....... *G01N 33/54333* (2013.01); *B01D 29/05* (2013.01); *G01N 33/54326* (2013.01); *G01N 33/57488* (2013.01); *G01N 2458/00* (2013.01)

(58) Field of Classification Search
None
See application file for complete search history.

(56) References Cited

U.S. PATENT DOCUMENTS

| | | | |
|---|---|---|---|
| 5,788,819 A | 8/1998 | Onishi et al. | |
| 5,972,721 A * | 10/1999 | Bruno | B03C 1/01 209/213 |
| 6,268,119 B1 | 7/2001 | Sumita et al. | |
| 6,374,684 B1 * | 4/2002 | Dority | B01L 3/502 73/864.81 |
| 6,391,541 B1 * | 5/2002 | Petersen | B01L 3/502 435/5 |
| 8,679,751 B2 * | 3/2014 | Huang | B01L 3/5021 435/6.1 |
| 10,093,919 B2 * | 10/2018 | Holmberg | B01L 3/5025 |
| 2004/0195099 A1 * | 10/2004 | Jacobson | G01N 27/44743 204/450 |

(Continued)

FOREIGN PATENT DOCUMENTS

EP    1151297    11/2001
EP    2853893 A1    4/2015

(Continued)

OTHER PUBLICATIONS

Extended European Search Report issued in corresponding European Patent Application No. 17194248.5 dated Jan. 3, 2018.

(Continued)

*Primary Examiner* — Gailene Gabel
(74) *Attorney, Agent, or Firm* — Morgan, Lewis & Bockius LLP

(57) ABSTRACT

The present disclosure relates to a method for labeling particles with magnetic particles and an apparatus for labeling particles with magnetic particles.

13 Claims, 4 Drawing Sheets

(56) References Cited

U.S. PATENT DOCUMENTS

| | | | |
|---|---|---|---|
| 2011/0014646 A1 | 1/2011 | Fukuda et al. | |
| 2011/0014685 A1 | 1/2011 | Fukuda et al. | |
| 2015/0087016 A1 | 3/2015 | Takagi | |
| 2016/0237397 A1* | 8/2016 | Guia | C12M 23/20 |
| 2017/0248508 A1* | 8/2017 | Ward | G01N 15/1404 |

FOREIGN PATENT DOCUMENTS

| | | |
|---|---|---|
| EP | 3072578 A1 | 9/2016 |
| EP | 3176267 A1 | 6/2017 |
| JP | H06-201698 A | 7/1994 |
| JP | H10-201470 A | 8/1998 |
| JP | 2009-511001 A | 3/2009 |
| JP | 2015-087382 A | 5/2015 |
| WO | 00/45169 A1 | 8/2000 |
| WO | 2007/035498 A2 | 3/2007 |

OTHER PUBLICATIONS

Xu et al., "A Filtration-Based Protein Microarray Technique," Analytical Chemistry, 75: 5345-5351 (2003).

Aubert et al., "Rapid detection of toxoplasmic nucleic acid by enzyme-linked immunofiltration-assay after membrane transfer," Electrophoresis, 16: 354-356 (1995).

Office Action issued in corresponding European Patent Application No. 17194248.5 dated Nov. 22, 2018.

Ozkumur et al., "Inertial Focusing for Tumor Antigen-Dependent and -Independent Sorting of Rare Circulating Tumor Cells," Science Translational Medicine, 5: 179ra47 (2013).

Office Action issued in corresponding European Patent Application No. 17194248.5 dated Apr. 16, 2019.

Office Action issued in corresponding Japanese Patent Application No. 2017-188908 dated Apr. 9, 2020.

* cited by examiner

METHOD FOR MAGNETICALLY LABELING PARTICLES AND LABELING APPARATUS

BACKGROUND OF THE INVENTION

1. Field of the Invention

The present disclosure relates to a method for labeling particles with magnetic particles (hereinafter also referred to as "magnetic beads") and an apparatus for labeling particles with magnetic particles. The present disclosure, for example, relates to a method for magnetically labeling particles captured by a filter with magnetic beads at the filter and a labeling apparatus used therefor.

2. Description of Related Art

Examples of a method for separating particles included in a suspension, specifically rare cells in a biological sample, include magnetic separation and size separation. Magnetic separation is a method that depends on proteins expressed in cells that are to be separated. On the other hand, size separation is a method that utilizes the size of particles or a difference in deformability.

Either one of these techniques is used in a common method for separating rare cells. As a method using size separation, for example, a method has been developed in which a filter having a predetermined property is used.

On the other hand, in recent years, from the viewpoint of increasing precision in separation of rare cells, it has been proposed that magnetic separation and size separation, which are separation methods having different principles, are used in combination.

SUMMARY OF THE INVENTION

Examples of rare cells include circulating tumor cells (CTCs) and medically important cells such as immune cells, in addition to CTCs. One example of the CTCs is cancer cells that separate from primary tumor tissues or metastatic tumor tissues. These cancer cells are said to metastasize by being carried to other organs or the like through blood or lymphatic vessels. Also, CTCs in blood are recognized as useful as a factor for determining the effect of treating a metastatic cancer or predicting prognosis of a metastatic cancer, and thus CTCs have been analyzed proactively.

However, 10 mL of blood contains only about 0 to 10 rare cells such as CTCs, and thus, in order to perform more accurate analysis, rare cells need to be separated from a specimen or concentrated with high precision.

In one aspect, according to some embodiments of the disclosure herein, rare cells may be efficiently separated from blood using a filter having a predetermined property. However, in addition to rare cells, blood contains a large amount of blood cell components such as red blood cells and white blood cells (about several hundred billions of red blood cells, and about tens of millions of white blood cells). In particular, the size of white blood cells is almost equal to or larger than the size of rare cells, and thus white blood cells are sometimes captured together with rare cells even though the above-described filter is used.

The inventors found that when white blood cells are captured together with rare cells, the following two problems occurred, for example. First, because blood (the specimen) contains a small amount of rare cells but contains a large amount of white blood cells, the amount of white blood cells captured by the filter is larger than the number of rare cells, and thus part of the white blood cells are detected as rare cells, as a result of which false-positive occurs easily. Second, when rare cells are subjected to specific gene mutation detection, only genotypes of white blood cells, which are not the rare cells, are detected, and as a result, false-negative occurs easily.

In view of these problems, it is necessary to efficiently separate white blood cells and rare cells that are captured by the filter.

In one or more embodiments, the present disclosure provides a labeling method and a labeling apparatus with which particles captured by a filter may be efficiently magnetically labeled at the filter.

In one aspect, the present disclosure relates to a method for labeling particles captured by a filter with magnetic beads at the filter, the magnetically labeling method including supplying a suspension containing magnetic beads to one surface of the filter, the one surface on which particles are captured, creating a state in which liquid containing the magnetic beads is in contact with both surfaces of the filter, by passing a portion of the suspension the filter from the one surface of the filter toward the other surface of the filter, and reversely passing liquid containing the magnetic beads through the filter from the other surface of the filter toward the one surface of the filter.

In one aspect, the present disclosure relates to an apparatus for labeling particles with magnetic beads, the labeling apparatus including a filter portion capable of holding a filter, an introduction flow channel through which a suspension containing magnetic beads may be introduced into the filter portion, an ejection flow channel capable of holding or ejecting liquid that has passed through the filter portion, a liquid feeding means capable of supplying the suspension to the filter portion, and a control unit that controls the liquid feeding means, in which the control unit controls the liquid feeding means so as to pass a portion of the suspension through the filter from one surface of the filter to the other surface of the filter so as to create a state in which liquid containing the magnetic beads is in contact with both surfaces of the filter, and to reversely pass liquid containing the magnetic beads through the filter from the other surface of the filter to the one surface of the filter.

According to the present disclosure, in one aspect, particles captured by a filter may be efficiently labeled with magnetic beads at the filter.

DETAILED DESCRIPTION OF THE INVENTION

Figure 1:
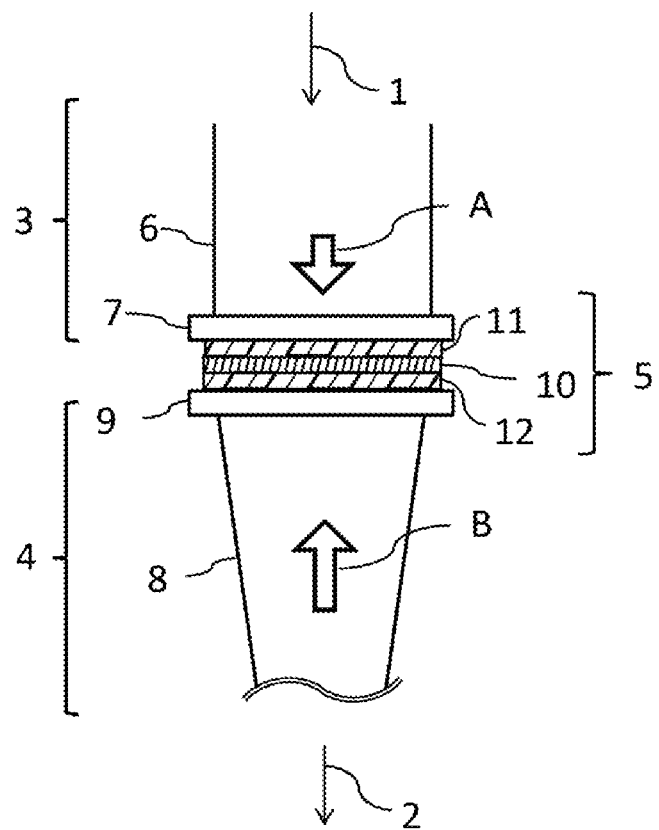
FIG. 1 shows one example of a cell labeling apparatus that will be used in a magnetically labeling method of the present disclosure.

Rare cells such as circulating tumor cells (CTCs) are sometimes present in blood. CTCs are cells that separate from primary tumor tissues or metastatic tumor tissues and invade blood. Because cancer metastasis is thought to be caused by cancer cells being carried to other sites in a body through blood vessels or lymph vessels and proliferating, it has been reported that the number of CTCs in blood relates to the possibility of cancer metastasis and prognosis. Also, rare cells include medically important cells such as immune cells, in addition to CTCs. Thus, it is predicted that rare cells in blood will be further actively analyzed hereafter.

In general, 10 mL of blood contains about several hundred billions of red blood cells and about tens of millions of white blood cells, and only about 0 to 10 rare cells such as CTCs. Thus, in order to perform more accurate analysis, it is necessary to highly precisely separate and collect rare cells from a specimen such as blood.

Rare cells include not only cancer cells that are larger than blood cells but also small cells and cells having high deformability. An example of the small cells is human colon cancer cells, including commercially available SW620 (cell line name is human colon cancer cell) that is confirmed as a small cell. An example of the cell having high deformability is human cancer cells, including commercially available SNU-1 (cell line name is human cancer cell) that is confirmed as a cell having high deformability.

The applicant established a method with which small cells and cells having high deformability may be captured at a high capture ratio with use of a predetermined filter.

However, as described above, even though specimens such as blood are separated using this filter, white blood cells included in the specimens in a large amount are captured together with rare cells in some cases. Thus, treatment for further separating rare cells and white blood cells is required. Also, in order to analyze the separated rare cells, various treatments need to be performed.

On the other hand, as described above, an extremely small number of rare cells are present in a specimen, and thus loss of cells in treatments such as separation with a filter and labeling, and loss of cells at the time of collection need to be avoided as much as possible. Thus, it has been proposed that various treatments for separation and analysis above are performed in a state in which the cells are captured by the filter. Treatment at the filter is performed by supplying various treatment liquids to the filter so as to react with cells, and then removing unreacted treatment liquids by passing the liquids through the filter. That is, the filter has a function as a reaction field for B/F separation (bound/free separation), and is capable of performing various treatments without loss of cells.

The inventors found that in various treatments at the filter, those various treatments were problematic in that there were treatments with which sufficient treatment effect was obtained and treatments with which sufficient treatment effect was not obtained. Specifically, although antibody staining may sufficiently stain cells, labeling with magnetic particles has extremely low labeling efficiency, which is problematic in that cells cannot be magnetically labeled sufficiently.

In view of the above-described problems, attempts were made to collect cells such as rare cells from the filter and label the collected cells with magnetic particles, but this method was problematic in that the degree of the occurrence of loss of rare cells captured by the filter was significant between workers, experiments, or the like, and the reproducibility was low. Also, after labeling treatment was performed, excess unreacted magnetic particles and cells were not sufficiently separated from each other. As a result, there were problems that at the time of magnetic separation, which is the latter treating step, rare cells were caught in excess magnetic particles that were present in a large amount and were magnetically separated together with those magnetic particles, as a result of which separation precision decreased.

In one aspect, when cells are labeled with magnetic particles in a state in which cells are captured by a filter, the efficiency of labeling cells with magnetic particles may be increased, and cells and excess magnetic particles that are present in a large amount may be separated by passing a suspension containing magnetic particles through the filter such that the entire filter on which cells are captured is covered by the suspension containing magnetic particles, and then passing liquid containing magnetic particles that was included in the suspension through the filter in a direction that was opposite to the direction in which the suspension was fed, which may be referred to as reversely passing.

In one aspect, the number of white blood cells is larger than the number of rare cells captured by the filter, and thus if white blood cells, which are the cells that are not to be collected and thus are not the target cells, are labeled with magnetic particles, precision in separation of rare cells may be increased. For example, the CTCs, which are rare cells, include a group in which epithelial cell antigens such as EpCAM and cytokeratin are expressed and a group in which epithelial mesenchymal transition occurs in which expression of these epithelial markers decreases and a mesenchymal cell antigen such as Vimentin is expressed. Thus, it is difficult to recognize all of the CTCs with a specific antigen. Thus, by labeling white blood cells, which are known to have a specific antigen, with magnetic particles instead of CTCs and separating the white blood cells, all of the CTCs may be collected without antigens while precision in separation of CTCs and white blood cells may be increased. The object to be labeled in analysis of rare cells such as CTCs in the present disclosure is not limited to white blood cells, and may be rare cells.

The mechanism with which cells captured by a filter may be efficiently labeled with magnetic particles at the filter by the present disclosure is not clear, but it is inferred as follows.

When whole blood is fed to a filter having a plurality of through holes and filtered, whole blood is fed as laminar flow, and thus the flow velocity decreases in the vicinity of a wall surface of the flow channel, and as a result of which, a relatively large amount of red blood cells and white blood cells, which are not to be captured (are not the target cells), remain on the filter near the wall surface without being filtered. When staining treatment or labeling treatment is performed in this state, an antibody staining liquid, which is a soluble reagent, may perform sufficient staining due to dispersion of the reagent, but labeling with magnetic particles cannot sufficiently bring magnetic particles into contact with white blood cells near the wall surface and has low labeling efficiency. It is conceivable that the reason for this is that the flow velocity is lower near the wall surface on which multiple white blood cells are present compared to the central portion of the filter, and magnetic particles disperse relatively moderately. In contrast, in the method of the present disclosure, a suspension is fed and then reversely fed such that both main surfaces of the filter are in contact with liquid containing magnetic particles. By immersing both main surfaces of the filter in the liquid containing magnetic particles, cells captured by the filter may come into contact with both a surface of the filter that captures cells, which is referred to as cell capture surface, and a surface of the filter that is opposite to the cell capture surface, which is an upper surface of the filter and/or a lower surface of the filter, and may come into contact with the suspension in the through holes, and thus the surface area of cells that are in contact with the suspension, for example, of magnetic particles, increases significantly. By reversely feeding the suspension in this state from the surface of the filter that is opposite to the capture surface of the filter toward the cell capture surface, for example, from the lower surface of the filter toward the upper surface, cells that fit in the through holes of the filter separate therefrom and the suspension containing magnetic particles is stirred due to turbulent flow caused by this reverse liquid feeding, and thereby the frequency at which cells and magnetic particles come into contact with each other further increases. The efficiency of labeling with magnetic particles may be increased as a result of these mechanisms. However, the present disclosure need not be interpreted as being limited to these mechanisms.

Method for Labeling with Magnetic Beads

In one aspect, the present disclosure relates to a method for labeling particles captured by a filter with magnetic beads at the filter. In one aspect, the labeling method of the present disclosure includes supplying a suspension containing magnetic beads to one surface of the filter, the one surface on which particles are captured, creating a state in which liquid containing the magnetic beads is in contact with both surfaces of the filter, by passing a portion of the suspension through the filter from the one surface of the filter toward the other surface of the filter, and reversely passing liquid containing the magnetic beads through the filter from the other surface of the filter toward the one surface of the filter. Also, in one aspect, the labeling method of the present disclosure includes supplying the suspension containing magnetic beads onto an upper surface of the filter on which the particles are captured, passing a portion of the suspension through the filter toward a lower surface side of the filter such that an upper liquid surface and a lower liquid surface of the suspension sandwich the filter, and passing the suspension through the filter from the lower surface side of the filter toward an upper surface side. According to the labeling method of the present disclosure, in one or more embodiments, particles captured by a filter may be efficiently labeled with magnetic beads at the filter without being collected from the filter.

The labeling method of the present disclosure includes supplying a suspension containing magnetic beads onto the surface of the filter on which particles are captured.

There is no particular limitation on the amount of supply of the suspension containing magnetic beads, and it may be determined as appropriate in accordance with the filtering area of the filter or the like. In one or more embodiments, from the viewpoint of being capable of uniformly suspending magnetic beads at the filter efficiently, the supply amount is about 50 μL or more, 80 μL or more or 100 μL or more per filtering area (e.g., 28 mm$^2$), or from the viewpoint of being capable of uniformly suspending magnetic beads with a small amount of liquid efficiently, the supply amount is about 500 μL or less, 400 μL or less or 300 μL or less per filtering area (e.g., 28 mm$^2$). As used herein, the term "about" may refer to a range of values that are similar to the stated reference value. In certain embodiments, the term "about" refers to a range of values that fall within 15, 10, 9, 8, 7, 6, 5, 4, 3, 2, 1 percent or less of the stated reference value.

In one or more embodiments, from the viewpoint of efficient reaction between magnetic beads and cells, the amount of magnetic beads (i.e., the concentration of the solid content) in the suspension containing magnetic beads is about 0.0025 wt % or more or 0.004 wt % or more, and from the viewpoint of suppressing nonspecific reaction between magnetic beads and cells, the amount of magnetic beads is about 0.0625 wt % or less or 0.0375 wt % or less.

There is no particular limitation on the magnetic beads or particles, and the magnetic beads or particles may be determined as appropriate in accordance with the types of particles that are to be labeled or the like. In one or more embodiments, known magnetic beads that are used to magnetically label particles such as cells, or magnetic beads that will be developed later may be used as the magnetic beads. In one or more embodiments, examples of the magnetic beads include magnetic particles or beads having surfaces on which substances that specifically react with binding molecules of the particles that are to be labeled are fixed. In one or more embodiments, examples of this substance include avidin, streptavidin, neutravidin, an antibody, and an antigen. There is no particular limitation on the size of the magnetic bead, and the size of the magnetic bead may be determined as appropriate in accordance with the size of particles and/or the size of opening portions (holes) of the filter. If the diameter of a particle to be labeled is 5 to 20 μm, such as white blood cells or CTCs, in one or more embodiments, the size of the magnetic bead is about 1 μm or less, 0.8 μm or less, or 0.5 μm or less from the viewpoint of increasing the efficiency of labeling. From the viewpoint of increasing magnetic separation efficiency, the size of the magnetic bead is about 0.05 μm or more or 0.1 μm or more. From the viewpoint of being capable of removing the excess magnetic beads by washing after labeling, the size of the magnetic bead is smaller than the size of opening portions (holes) of the filter.

The labeling method of the present disclosure includes feeding a portion of the suspension supplied to the surface of the filter at which particles are captured, which is the particle capture surface or the upper surface of the filter, toward the other surface of the filter, which may be the surface of the filter that is opposite to the particle capture surface, including the opposite surface or the lower surface of the filter, and creating a state in which liquid containing magnetic beads is in contact with both surfaces of the filter, which are the particle capture surface and the opposite surface. Also, in one or more embodiments, feeding of the suspension may include passing a portion of the suspension through the filter toward the lower surface side of the filter such that the upper liquid surface and the lower liquid surface of the liquid containing magnetic beads sandwich the filter. In one or more embodiments, this liquid feeding may be performed such that liquid containing magnetic beads is held in the vicinity of the opposite surface of the filter. In one or more embodiments, this feeding may be performed by drawing the suspension with a pump from the opposite surface side such that the suspension passes through the filter and the liquid containing magnetic beads comes into contact with both surfaces of the filter. That is, with the labeling method of the present disclosure, a portion of the suspension is positively passed through the filter toward the surface of the filter that is opposite to the particle capture surface, and this is different from a phenomenon in which liquid unintentionally permeates or diffuse through the filter and reaches the vicinity of the lower surface of the filter.

There is no particular limitation on the liquid containing magnetic beads as long as the liquid contains magnetic beads, and in one or more embodiments, examples of the liquid include a suspension containing magnetic beads that is supplied to the surfaces of the filter, and a liquid obtained by mixing and diluting this suspension with another liquid. In one or more embodiments, the concentration of magnetic beads, or in terms of the concentration of the solid content in the liquid containing magnetic beads is about 0.00009 wt % or more, 0.00012 wt % or more, or 0.00021 wt % or more, and 0.0581 wt % or less, 0.0415 wt % or less, or 0.00249 wt % or less. In one or more embodiments, examples of the other liquid include phosphate-buffered saline (PBS), PBS-BSA (for example, 0.2%), PBS-EDTA (for example, 1 mg/ml), and buffer solutions, isotonic solutions, and aqueous solvents such as water. In one or more embodiments, examples of the buffer solutions include Tris buffer solutions such as a Tris-HCl buffer solution, phosphate buffer solutions, HEPES buffer solutions, and citrate-phosphate buffer solutions. Also, examples of the isotonic solutions include physiological saline, a sucrose isotonic solution, a glucose isotonic solution, and a mannose isotonic solution.

In one or more embodiments, from the viewpoint of both surfaces of the filter sufficiently coming into contact with the liquid containing magnetic beads, the ratio of the suspension that is passed through the filter toward the opposite surface side is about 10% or more, 20% or more, or 40% or more of the suspension that is supplied to the particle capture surface, and from the viewpoint of efficiently feeding the whole suspension when the suspension is supplied from the opposite surface side toward the particle capture surface side, the ratio is about 90% or less, 80% or less, or 60% or less.

In one or more embodiments, from the viewpoint of increasing the efficiency of reaction between particles captured by the filter and magnetic beads, the flow velocity of the suspension is about 0.07 mm/sec or more, 0.1 mm/sec or more, or 0.3 mm/sec or more per opening area of the filter, and/or similarly, from the viewpoint of increasing the efficiency of reaction between particles captured by the filter and magnetic beads, the flow velocity is about 14 mm/sec or less, 1.4 mm/sec or less, or 0.7 mm/sec or less per opening area of the filter. From the viewpoint of increasing the efficiency of reaction between particles captured by the filter and magnetic beads, the flow rate of the suspension is about 0.05 µL/min or more, 0.1 µl/min or more, or 0.2 µL/min or more, and/or similarly, from the viewpoint of increasing the efficiency of reaction between particles captured by the filter and magnetic beads, the flow rate is about 10000 µL/min or less, 1000 µl/min or less, or 500 µl/min or less. "Flow rate per opening area of the filter" in the present disclosure refers to the velocity of liquid passing through opening portions or holes of the filter. In one or more embodiments, the flow velocity per opening area may be calculated by dividing the flow rate of the whole system by the total area of the opening portions or holes. "Flow rate" in the present disclosure refers to the amount or volume of liquid that flows per unit of time. In one or more embodiments, an example of the flow rate is the amount or volume of liquid that passes through the filter per unit of time.

The labeling method of the present disclosure includes passing liquid located on the side of the lower surface through the filter from the surface side of the filter that is opposite to the particle capture surface toward the surface side of the filter on which particles are captured, for example, from the lower surface side of the filter toward the upper surface side, causing backflow. The reactivity between magnetic beads and particles that are to be labeled and the labeling efficiency may be increased by passing the liquid through the filter in a state in which both main surfaces are in contact with liquid containing magnetic beads in an immersed state from the opposite surface side toward the particle capture surface side so as to separate the particles captured by the filter from the filter while reversely feeding the suspension containing magnetic beads.

In one or more embodiments, backflow may occur by feeding only a suspension located on the side of the surface of the filter that is opposite to the particle capture surface, or may occur by feeding liquid that is different from the suspension, which may be the side of the lower surface of the filter. In one or more embodiments, examples of the liquid that is different from the suspension include phosphate-buffered saline (PBS), PBS-BSA (for example, 0.2%), PBS-EDTA (for example, 1 mg/ml), and buffer solutions, isotonic solutions, and aqueous solvents such as water. In one or more embodiments, examples of the buffer solutions include Tris buffer solutions such as a Tris-HCl buffer solution, phosphate buffer solutions, HEPES buffer solutions, and citrate-phosphate buffer solutions. Also, examples of the isotonic solutions include physiological saline, a sucrose isotonic solution, a glucose isotonic solution, and a mannose isotonic solution.

In one or more embodiments, the flow velocity of feeding from the opposite surface side to the particle capture surface side, which is referred to as the flow velocity of backflow, may be determined as appropriate by the flow velocity of a specimen when particles are captured by the filter. In one or more embodiments, the flow velocity of backflow may be faster than the flow velocity of the specimen or slower than the flow velocity of the specimen. In one or more embodiments, examples of the flow velocity of backflow include a factor of about $1/10$ or more, $1/5$ or more, $1/2$ or more, 1 or more, 2 or more, 3 or more, or 5 or more, with respect to the flow velocity of the specimen. In one or more embodiments, the flow velocity of backflow is faster than the flow velocity of the specimen from the viewpoint of increasing the efficiency of labeling with magnetic beads.

In one or more embodiments, from the view point of further increasing the efficiency of labeling with magnetic beads, the flow velocity of backflow from the opposite surface side to the particle capture surface side is about 0.01 mm/sec or more, 0.1 mm/sec or more, or 1 mm/sec or more per opening area of the filter, and/or from the viewpoint of suppressing damage to cells, the flow velocity of liquid feeding is about 150000 mm/sec or less, 100000 mm/sec or less, or 50000 mm/sec or less per opening area of the filter. From the viewpoint of increasing the efficiency of labeling with magnetic beads, the flow rate of backflow is about 10 µL/min or more, 100 µL/min or more, or 1000 µL/min or more, and/or from the viewpoint of suppressing damage to cells, the flow rate of backflow is about 100 million µl/min or less, 50 million µL/min or less, or 10 million µL/min or less.

In one or more embodiments, from the viewpoint of efficiently feeding liquid containing magnetic beads to the particle capture surface, the amount of liquid that is caused to reversely feed, which is referred to as backflow, is about 50 µL or more or 1000 µL/or more per filtering area (e.g., 28 mm$^2$), and from the viewpoint of maintaining the concentration of the suspension, the amount of liquid is about 1000 µL or less, 500 µL or less, or 300 µL or less.

There is no particular limitation on the number of instances of immersion of the filter in the suspension and liquid feeding from the above-described opposite surface side to the particle capture surface side or backflow. The number of instances thereof may be one, or two or more.

In one or more embodiments, from the viewpoint of further increasing the efficiency of labeling with magnetic beads, the labeling method of the present disclosure may include stirring the liquid containing magnetic beads on the particle capture surface and particles that are to be labeled after the above-described backflow. In one or more embodiments, stirring is performed through pipetting, for example.

From the viewpoint of further increasing the efficiency of labeling with magnetic beads, in one or more embodiments, the labeling method of the present disclosure may include letting the liquid stand still after stirring. In one or more embodiments, from the viewpoint of sufficient reaction between particles and magnetic beads, the standing period of time is about 1 minute or more, 5 minutes or more, or 10 minutes or more, and/or from the viewpoint of preventing nonspecific reaction between particles and magnetic beads, the standing period of time is about 60 minutes or less, 45 minutes or less, or 30 minutes or less.

From the viewpoint of further increasing the efficiency of labeling with magnetic beads, in one or more embodiments, the labeling method of the present disclosure may include filtering, through a filter, the liquid containing magnetic beads and particles that are to be labeled after pipetting and letting the liquid stand still thereafter. Accordingly, particles that were pre-captured by the filter including particles that are to be labeled may be captured by the filter again and these particles and magnetic beads may be brought into contact with each other again. In one or more embodiments, it is preferable to let the liquid stand still in a state in which both surfaces of the filter are covered with the liquid containing magnetic beads and particles that are to be labeled.

In one or more embodiments, from the viewpoint of increasing the efficiency of reaction between particles captured by the filter and magnetic beads, the flow velocity of liquid feeding for filtering is about 0.07 mm/sec or more, 0.1 mm/sec or more, or 0.3 mm/sec or more per opening area of the filter, and/or similarly, from the viewpoint of increasing the efficiency of reaction between particles captured by the filter and magnetic beads, the flow velocity is about 14 mm/sec or less, 1.4 mm/sec or less, or 0.7 mm/sec or less per opening area of the filter. From the viewpoint of increasing the efficiency of reaction between particles captured by the filter and magnetic beads, the flow rate of the suspension is about 0.05 μL/min or more, 0.1 μL/min or more, or 0.2 μL/min or more, and/or similarly, from the viewpoint of increasing the efficiency of reaction between particles captured by the filter and magnetic beads, the flow rate is about 10000 μL/min or less, 1000 μL/min or less, or 500 μL/min or less.

In one or more embodiments, from the viewpoint of sufficient reaction between particles and magnetic beads, the standing period of time is about 1 minute or more, 5 minutes or more, or 10 minutes or more, and/or from the viewpoint of preventing nonspecific reaction between particles and magnetic beads, the standing period of time is about 60 minutes or less, 45 minutes or less, or 30 minutes or less.

In one or more embodiments, the labeling method of the present disclosure may include feeding washing liquid for washing excess magnetic beads that were not used in labeling. In one or more embodiments, examples of the washing liquid include phosphate-buffered saline (PBS), PBS-BSA (for example, 0.2%), PBS-EDTA (for example, 1 mg/ml), and buffer solutions, isotonic solutions, and aqueous solvents such as water. In one or more embodiments, examples of the buffer solutions include Tris buffer solutions such as a Tris-HCl buffer solution, phosphate buffer solutions, HEPES buffer solutions, and citrate-phosphate buffer solutions. Also, examples of the isotonic solutions include physiological saline, a sucrose isotonic solution, a glucose isotonic solution, and a mannose isotonic solution.

In one or more embodiments, the labeling method of the present disclosure may include capturing the particles using the filter before the suspension containing magnetic beads is supplied. In one or more embodiments, the capturing particles by the filter may be carried out by supplying a specimen containing particles that are to be labeled to the filter and filtering the specimen through the filter.

From the viewpoint of increasing the ratio of capturing particles in the specimen, in one or more embodiments, the flow velocity of the specimen is about 0.01 mm/sec or more, 0.05 mm/sec or more, or 0.1 mm/sec or more per opening area, and/or from a similar point, the flow velocity of the specimen is about 100 mm/sec or less, 50 mm/sec or less, 25 mm/sec or less, 10 mm/sec or less, 5 mm/sec or less, or 2 mm/sec or less. From the viewpoint of increasing the ratio of capturing particles in the specimen, in one or more embodiments, the flow rate of the specimen is about 0.01 ml/min or more, 0.05 ml/min or more, or 0.1 ml/min or more, and/or from a similar point, the flow rate of the specimen is 100 ml/min or less, 50 ml/min or less, 25 ml/min or less, or 10 ml/min or less.

In one or more embodiments, the labeling method of the present disclosure may include filling a flow channel on the side of a filter surface that is opposite to the filter surface on which particles are captured, with liquid before the suspension containing magnetic beads is supplied. In one or more embodiments, the flow channel may be filled with liquid by immersing the filter on which particles are captured in this liquid. In one or more embodiments, liquid that may be used as the above-described washing liquid may be used as the liquid.

In one or more embodiments, the labeling method of the present disclosure may be performed using an apparatus having a separation portion provided with a filter having a plurality of through holes or the like. From the viewpoint of being capable of increasing operability and efficiently performing labeling with a small amount of a magnetic bead suspension, in one or more embodiments, the labeling method of the present disclosure may be performed with an open-system apparatus in which the upper portion of a filter is open.

In one or more embodiments, the above-described treatments such as supply, feeding, and stirring of the suspension in the labeling method of the present disclosure may be performed automatically or manually. Also, a portion of the treatments may be performed manually and the remaining treatments may be performed automatically.

In one or more embodiments, an example of the filter used in the labeling method of the present disclosure is a filter that may capture rare cells in a specimen. In one or more embodiments, the filter may capture at least small cancer cells, cancer cells having high deformability, or both of these cancer cells. Also, in one or more embodiments, the filter may capture at least SNU-1, SW620, or both of these, and may capture CTCs in the specimen. In one or more embodiments, a conventionally known filter or a filter that will be developed later and may capture rare cells may be used as the filter. In one or more embodiments, examples of the filter include the filter disclosed in JP 2015-087382A and the filter disclosed in JP 2016-057313A, both of which are incorporated by reference herein in their entirety. Also, examples of the filter include a sheet-shaped single membrane including multiple through holes that are each an ellipse having a short axial diameter of about 1 μm to 50 μm, a perfect circle, a rectangle, or the like, and may be membranes other than nonwoven fabric.

In one or more embodiments, an example of the material of the filter is metal such as nickel, SUS, gold, silver, copper, aluminum, tungsten, or chromium.

There is no particular limitation on the filtering area, and in one or more embodiments, the filtering area is about 5 mm$^2$ or more or 10 mm$^2$ or more, and/or 2,000 mm$^2$ or less, 1,000 mm$^2$ or less, 500 mm$^2$ or less, 200 mm$^2$ or less, 150 mm$^2$ or less, 100 mm$^2$ or less, 80 mm$^2$ or less, 50 mm$^2$ or less, 40 mm$^2$ or less, 30 mm$^2$ or less, or 25 mm$^2$ or less. "Filtering area" in the present disclosure refers to the area of a portion of the entire area of the filter that comes into contact with the suspension containing magnetic beads or the specimen (to which liquid is fed).

In one or more embodiments, the particles labeled with the labeling method of the present disclosure may are separated using a known magnetic separation apparatus.

In one or more embodiments, the labeling method of the present disclosure may specifically label particles that are to be labeled in accordance with the property of particles or proteins expressed with particles even in a case where a plurality of types of particles are captured by the filter. In one or more embodiments, in the analysis of rare cells such as CTCs, even in a case where rare cells and white blood cells are captured by the filter, according to the labeling method of the present disclosure, white blood cells may be magnetically labeled at a high labeling efficiency. Thus, after labeling with the labeling method of the present disclosure, rare cells and magnetically labeled white blood cells may be precisely separated by magnetically separating the collected suspension, and thereby rare cells may be collected highly precisely. In one or more embodiments, in a case where rare cells and white blood cells are captured by the filter, rare cells may be magnetically labeled instead of white blood cells.

In one or more embodiments, the collection after labeling may be performed by passing a collection liquid through the filter in a direction that is opposite to a filtering direction when particles are captured by the filter. In one or more embodiments, similarly to a method for collecting cells, which will be described later, the collection may be performed by passing liquid in a direction that is reverse of the direction in which the specimen for capturing cells passes, through the filter on which cells were captured such that a ratio between the flow rate of the passing collection liquid and the flow rate of the passing specimen ([flow rate of collection liquid]/[flow rate of specimen]) is about 25 or more, or by passing liquid at a flow velocity of about 1 mm/sec or more per opening area. Specific conditions and the like are similar to those in the method for collecting cells, which will be described later.

There is no particular limitation on the particles in the present disclosure, and examples of the particles include human cells or cells of an animal other than a human. Examples of cells on which there are no particular limitation include rare cells, white blood cells, red blood cells, platelets, and undifferentiated cells thereof. The rare cells refer to cells other than blood cells, including red blood cells, white blood cells, and platelets, that may be included in human blood or the blood of an animal other than a human. In one or more embodiments, examples of rare cells include cells selected from the group consisting of cancer cells, circulatory tumor cells, vascular endothelial cells, vascular endothelial progenitor cells, cancer stem cells, epithelial cells, hematopoietic stem cells, mesenchymal stem cells, fetal cells, stem cells, undifferentiated white blood cells, undifferentiated red blood cells, and combinations thereof.

An example of the specimen in the present disclosure includes a sample that may contain particle cells that will be applied to the labeling method of the present disclosure. In one or more embodiments, an example of the specimen is a blood specimen. In non-limited one or more embodiments, examples of the blood specimen include blood and a dilution thereof from the viewpoint of easy and fast treatment and suppressing damage to rare cells in blood.

Labeling Apparatus

In one aspect, the present disclosure relates to an apparatus for labeling particles with magnetic beads. The labeling apparatus of the present disclosure includes a filter portion capable of holding a filter, an introduction flow channel through which a suspension containing magnetic beads may be introduced into the filter portion, an ejection flow channel capable of holding or ejecting liquid that has passed through the filter portion, a liquid feeding means capable of supplying a suspension to the filter portion, and a control unit that controls the liquid feeding means. In the labeling apparatus of the present disclosure, the control unit controls the liquid feeding means so as to feed the suspension such that at least a portion of the suspension that is supplied to the filter portion passes through the filter portion and is held, and so as to reversely feed liquid containing magnetic beads that has passed through the filter portion. According to the labeling apparatus of the present disclosure, the labeling method of the present disclosure may be performed easily.

In one or more embodiments, the labeling apparatus of the present disclosure may include a stirring means for stirring liquid on the surface of the filter or the vicinity thereof.

In one or more embodiments, the control unit may control the liquid feeding means so as to supply the specimen containing particles that are labeled, to the filter portion. The control unit may control the liquid feeding means so as to feed this specimen at a flow velocity of about 0.01 mm/sec to 100 mm/sec per opening area of the filter. The control unit may control the liquid feeding means such that the flow velocity of reverse liquid feeding is faster than 1/10 the flow velocity of the specimen. The control unit may control the liquid feeding means such that the flow velocity of reverse liquid feeding is about 0.01 mm/sec or more per opening area of the filter.

Hereinafter, one non-limited embodiment of the labeling method of the present disclosure will be described.

Description will be given using a rare cell labeling apparatus shown in FIG. 1.

FIG. 1 shows one example of the apparatus for labeling rare cells that may be utilized in the labeling method of the present disclosure.

The apparatus shown in FIG. 1 includes a supply port 1 for supplying a suspension containing magnetic beads, a washing liquid, a staining liquid, or the like, an ejection port 2 for ejecting waste liquid such as a washing liquid, or the like, a device upper portion 3, a device lower portion 4, a filter portion 5, and a liquid feeding mechanisms (not shown in the figure) capable of feeding liquid in an arrow A direction and an arrow B direction. The filter portion 5 is disposed between the device upper portion 3 and the device lower portion 4. The device upper portion 3 has a flow channel 6 and a support member 7 for fixing the filter portion 5, and the flow channel 6 is continuous with the supply port 1. The device lower portion 4 has a flow channel 8 and a support member 9 for fixing the filter portion 5, and the flow channel 8 is continuous with the ejection port 2. The filter portion 5 includes a filter 10 and bonding materials 11 and 12 for fixing the filter 10 (for example, double-sided tape or the like). The filter portion 10 is fixed to the device upper portion 3 and the device lower portion 4 by the bonding materials 11 and 12. The flow channel 6 that connects the supply port 1 and the filter portion 5 may be provided with a connection portion (not shown) and a three-way stopcock valve (not shown in the figure) that may switch liquids, in the upper portion of the filter portion 5. Also, the flow channel 6 that connects the supply port 1 and the filter portion 5 may be provided with a pressurizing means (not shown in the figure) to feed liquid at a constant pressure or at a constant flow rate, such that a constant pressure is applied to filtering. Also, liquid may be drawn with a syringe pump such that pressure applied to filtering does not reach a predetermined value or more.

Figure 2:
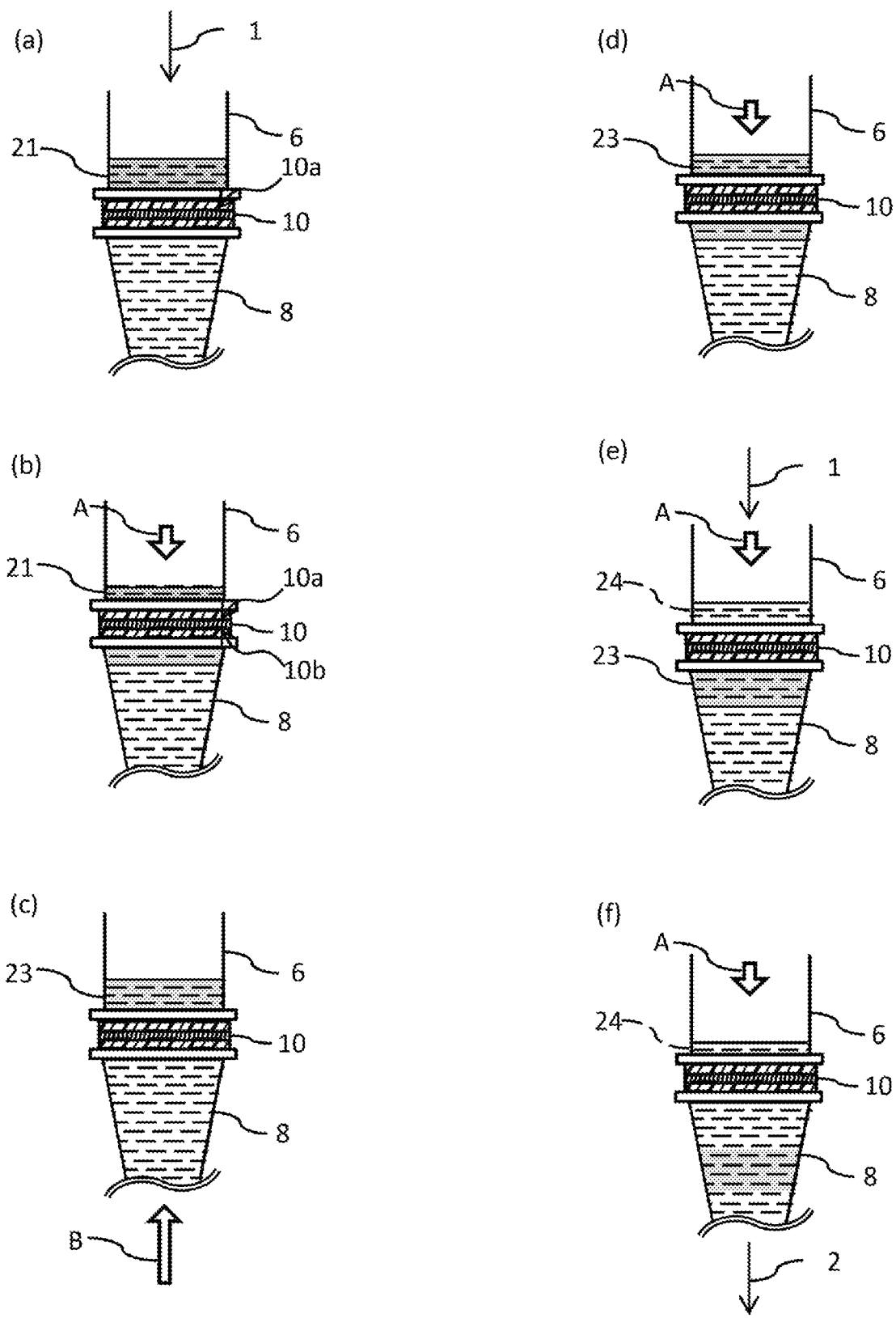
FIG. 2 shows a schematically illustrative diagram for illustrating one example of a procedure of the magnetically labeling method of the present disclosure.

Next, one example of the method for labeling particles using the apparatus shown in FIG. 1 will be described with reference to FIG. 2. In the present embodiment, an embodiment will be described as an example in which a filter capable of capturing rare cells is used as the filter and whole blood containing rare cells is filtered through this filter, and thereby white blood cells captured by the filter are labeled with magnetic beads. Also, a grey portion in FIG. 2 schematically shows a portion containing magnetic beads. The present disclosure is not limited to this embodiment.

First, a blood specimen is fed to a separation portion through the flow channel 6, and filtered through the filter 10. Accordingly, rare cells and white blood cells are captured by the filter 10.

Then, from the viewpoint of increasing reactivity of a reagent to white blood cells, red blood cells remaining on the filter 10 may be removed through treatment with supply of a hemolytic agent.

Next, the flow channel 8 is filled with a buffer solution by supplying the buffer solution from the supply port 1. The buffer solution is supplied such that a cell capture surface (the upper surface) 10a of the filter 10 is immersed therein. Next, a suspension 21 containing magnetic particles is supplied to the cell capture surface 10a of the filter 10 (FIG. 2(*a*)). From the viewpoint of increasing the reactivity between magnetic particles and white blood cells, white blood cells may be subjected to immunostaining with an antibody before supply of the suspension 21. Examples of the antibody include antibodies bound to binding molecules. In one or more embodiments, the binding molecule is biotin or the like. Also, for example, magnetic particles to which a substance that specifically reacts with the above-described binding molecules is fixed may be used as the magnetic particles. In one or more embodiments, examples of the specifically reacting substance include proteins such as streptavidin and neutravidin.

The suspension 21 is fed from the cell capture surface 10a side of the filter 10 toward a filter surface 10b side (in the arrow A direction shown in FIGS. 1 and 2) such that a portion of the suspension 21 containing magnetic particles moves toward the filter surface (the lower surface) 10b side (the flow channel 8 side) that is opposite to the cell capture surface 10a.

Next, liquid is fed (reversely fed) from the filter surface 10b side to the cell capture surface 10a side (in the arrow B direction shown in FIGS. 1 and 2) (FIG. 2(*c*)). Accordingly, liquid containing magnetic particles on the cell capture surface 10a of the filter 10 is stirred while cells that separate from the filter 10 are stirred on the cell capture surface (the upper surface) 10a of the filter 10, and as a result of which, it is possible to increase the frequency of contact between white blood cells and magnetic particles and to increase the labeling efficiency. The liquid feeding (reversely fed) may be performed by feeding only a suspension located on the filter surface 10b side, or by feeding the suspension located on the filter surface 10b side and liquid that is different from the suspension. The liquid that is different from the suspension may or may not contain magnetic particles.

Next, on the cell capture surface 10a of the filter 10, the suspension containing magnetic particles and cells is stirred with a pipette or the like, and then is allowed to stand still for a predetermined period of time. Accordingly, it is possible to further increase the frequency of contact between white blood cells and magnetic particles and to increase the labeling efficiency.

Next, a suspension 23 containing cells and magnetic particles on the cell capture surface 10a of the filter 10 is fed again from the cell capture surface 10a side to the filter surface 10b side that is opposite to the cell capture surface 10a (in the arrow A direction shown in FIGS. 1 and 2), and then is allowed to stand still for a predetermined period of time (FIG. 2(*d*)). Accordingly, cells included in the suspension are captured by the filter 10. Also, magnetic particles pass through the filter 10 and may be brought into contact with cells captured by the filter 10 again when passing through the filter 10, and thus it is possible to further increase the frequency of contact between white blood cells and magnetic particles and to increase the labeling efficiency. This liquid feeding may be performed such that the cell capture surface 10a of the filter 10 and the filter surface 10b that is opposite thereto are sandwiched by liquid containing magnetic particles.

Then, after the liquid 23 containing magnetic particles is lowered near the cell capture surface 10a of the filter 10, a washing liquid 24 is supplied from the cell capture surface 10a side of the filter 10, for example, in the arrow A direction shown in FIGS. 1 and 2 (FIG. 2(*e*)), and the washing liquid 24 is fed such that the liquid surface of the washing liquid 24 comes close to the cell capture surface 10a of the filter 10 (FIG. 2(*f*). Accordingly, unreacted magnetic particles remaining on the filter 10 are removed. Feeding of the washing liquid 24 may be repeated a plurality of times.

After white blood cells are labeled with the above-described magnetic particles, rare cells may be subjected to immunostaining with an antibody. Accordingly, rare cells resulting from separation and collection may be detected efficiently. Examples of the antibody include antibodies that recognize antigens expressed in CTCs, such as Cytokeratin. From the viewpoint of causing antibodies to react with antigens in rare cells, fixation treatment and membrane permeation treatment may be performed before labeling with the antibodies.

Lastly, a collection liquid containing cells (white blood cells and rare cells) captured by the filter 10 is pushed above the cell capture surface 10a by feeding a collection liquid from the filter surface 10b side (in the arrow B direction shown in FIGS. 1 and 2), and the liquid is collected with a pipette or the like. White blood cells labeled with magnetic particles and rare cells may be separated through separate magnetic separation of the collected collection liquid.

The present disclosure relates to one or more embodiments below.

[1] A method by which particles captured by a filter having a plurality of through holes are labeled with magnetic particles, the method including:

supplying a suspension containing magnetic particles onto a surface of the filter on which particles are captured;

creating a state in which liquid containing the magnetic particles is in contact with both surfaces of the filter by feeding a portion of the suspension from the surface of the filter toward another surface of the filter; and reversely feeding the liquid containing the magnetic particles from the other surface of the filter toward the surface of the filter on which the particles are captured.

[2] The labeling method according to [1], including stirring the liquid containing the magnetic particles on the surface of the filter on which the particles are captured, after the liquid is fed from the other surface of the filter to the surface of the filter on which the particles are captured.

[3] The labeling method according to [1] or [2], including letting the filters by feeding a specimen containing the particles to the filter.

[4] The labeling method according to [3], in which a flow velocity of the specimen is 0.01 mm/sec to 100 mm/sec per opening area of the filter.

[5] The labeling method according to [3] or [4], in which a flow velocity of the reverse liquid feeding is faster than 1/10 the flow velocity of the specimen.

[6] The labeling method according to any of [1] to [5], in which a flow velocity of the reverse liquid feeding is 0.01 mm/sec or more per opening area of the filter.

Also, the present disclosure provides an apparatus below, in addition to the above-described method. It goes without saying that an apparatus below is clearly and sufficiently disclosed by those skilled in the art in the above description.

(A1) An apparatus for labeling particles captured by a filter having a plurality of through holes with magnetic particles, the apparatus including:

a means for supplying a suspension containing magnetic particles onto an upper surface of the filter on which the particles are captured;

a means for feeding a portion of the suspension toward a lower surface side of the filter such that an upper liquid surface and a lower liquid surface of the suspension sandwich the filter; and a means for feeding liquid to the filter from the lower surface side of the filter toward an upper surface side.

(A2) The labeling apparatus according to (A1), including a means for stirring a suspension on the upper surface of the filter after liquid is fed from the lower surface side of the filter to the upper surface side.

(A3) The labeling apparatus according to (A1) or (A2), including a means for feeding a specimen containing the particles to the upper surface of the filter.

(A4) The labeling apparatus according to (A3), in which the specimen feeding means feeds the specimen such that a flow velocity of the specimen is 0.01 mm/sec to 100 mm/sec per opening area of the filter.

(A5) The labeling apparatus according to (A3) or (A4), in which a means for feeding the liquid from the lower surface side of the filter toward the upper surface side such that the flow velocity of liquid feeding from the lower surface side of the filter to the upper surface side is faster than 1/10 the flow velocity of the specimen.

(A6) The labeling apparatus according to any of (A1) to (A5), in which a means for feeding the liquid from the lower surface side of the filter toward the upper surface side such that the flow velocity of liquid feeding from the lower surface side of the filter to the upper surface side is 0.01 mm/sec or more per opening area of the filter.

[B1] An apparatus for labeling particles with magnetic particles, including:

a filter portion capable of holding a filter;

an introduction flow channel through which a suspension containing magnetic particles is introduced into the filter portion;

an ejection flow channel capable of holding or ejecting liquid that has passed through the filter portion;

a liquid feeding means capable of supplying the suspension to the filter portion; and a control unit that controls the liquid feeding means, in which the control unit controls the liquid feeding means so as to feed a portion of the suspension from one surface of the filter to another surface of the filter so as to create a state in which liquid containing the magnetic particles is in contact with both surfaces of the filter, and so as to reversely feed liquid containing magnetic particles from the other surface of the filter.

[B2] The labeling apparatus according to [B1], including a means for stirring liquid.

[B3] The labeling apparatus according to [B1] or [B2], including a means for stirring liquid on the surface of the filter or in the vicinity of the surface of the filter.

[B4] The labeling apparatus according to any of [B1] to [B3], in which the control unit controls the liquid feeding means so as to supply the specimen containing the particles that are to be labeled to the filter portion.

[B5] The labeling apparatus according to [B4], in which the control unit controls the liquid feeding means so as to feed the specimen at a flow velocity of 0.01 mm/sec to 100 mm/sec per opening area of the filter.

[B6] The labeling apparatus according to [B4] or [B5], in which the control unit controls the liquid feeding means such that a flow velocity of the reverse liquid feeding is faster than 1/10 the flow velocity of the specimen.

[B7] The labeling apparatus according to any of [B1] to [B6], in which the control unit controls the liquid feeding means such that the flow velocity of the reverse liquid feeding is 0.01 mm/sec or more per opening area of the filter.

Method for Collecting Cells in Specimen

In order to highly precisely analyze rare cells, cells captured by a filter need to be collected highly precisely. In view of this, in another aspect, the present disclosure relates to a method with which cells captured by the filter may be collected from the filter at a high collection ratio.

As a method for separating or collecting a specific component from blood, for example, JP 2015-087382A discloses a method for treating blood with a filter having a predetermined characteristic, letting the filter capture rare cells in blood, and analyzing the rare cells.

Cells are collected from body fluid for purposes other than examination. For example, JP H10-201470A discloses a method for collecting target cells from body fluid such as bone marrow, for hematopoietic stem cell transplantation or the like. Examples in JP H10-201470A disclose a method in which bone marrow, peripheral blood, or the like is introduced into nonwoven fabric, white blood cells or CD34 positive cells are captured by the nonwoven fabric, a liquid having a viscosity of 17.2 mPa·s or more and 31.8 mPa·s or less is reversely fed, and thereby white blood cells or CD34 positive cells captured by the nonwoven fabric are collected.

However, with the method of JP H10-201470A, the viscosity of a collection liquid used for collection needs to be 5 mPa·s or more and 31.8 mPa·s or less, which is problematic in that there is a limitation on the composition used in the collection liquid. Also, as described above, JP H10-201470A is problematic in that the collected cells are unsuitable for analysis because the method of JP H10-201470A is a method for separating and collecting cells for hematopoietic stem cells transplantation or the like, the cells captured by a capture means are collected with a large amount of a collection liquid.

JP 2015-087382A does not disclose a technique for collecting rare cells captured by a filter.

As described above, the applicant established a method with which small cells such as SW620 and cells having high deformability, such as SNU-1, may be captured at a high capture ratio with use of a predetermined filter.

Meanwhile, rare cells are analyzed by observing rare cells, measuring the number of rare cells, measuring nucleic acids extracted from rare cells, or the like. In order to precisely perform these analyses, it is necessary to separate and collect rare cells captured by the filter from the filter.

In the process of repeated intensive study, the inventors found that when rare cells were collected from the filter on which the rare cells were captured, cells were collected with a small amount of a collection liquid at a high collection ratio by causing the collection liquid to flow backward such that the ratio of the flow rate of the passing collection liquid to the flow rate of the passing specimen when rare cells were captured ([flow rate of collection liquid]/[flow rate of specimen]) was 25 or more. Also, the inventors found that by causing the collection liquid to flow backward to the filter that captured rare cells at a flow velocity of 1 mm/sec or more per opening area of the filter, the cells that were captured by the filter were collected at a high collection ratio while suppressing damage to the cells.

The inventors found, as one of the reasons why rare cells that were captured by the filter were not collected with a small amount of the collection liquid at a high collection ratio, that rare cells and other cells that were mixed in therewith closed a portion of the holes when the rare cells are filtered or captured, and the filter at the time of collection had closed holes and non-closed holes, as a result of which, a pressing force caused by the passing collection liquid was not sufficiently applied to the rare cells that were captured by the closed holes. Moreover, the inventors found that by passing the collection liquid through the filter in a direction that was reverse of the direction in which the specimen for capturing cells passed, and setting its flow velocity to be equal to the flow velocity at which turbulent flow occurred on the filter surface, which is a surface of the filter that is opposite to the cell capture surface of the filter, that let the collection liquid pass through, and thereby rare cells that were captured by the filter were collected with a small amount of the collection liquid at a high collection ratio.

JP H10-201470A discloses that by letting 30 ml of the collection liquid whose viscosity exceeded 17 mPa·s pass through the filter at 100 ml/min, after 50 ml of peripheral whole blood passed through a filter made of polyester nonwoven fabric at a flow velocity of approximately 5 ml/min, cells that were captured by the filter were collected (Examples 1 to 5). On the other hand, the same literature discloses that when a collection liquid (physiological saline) having a viscosity of 1.0 mPa·s was used instead of the collection liquid having the above-described viscosity, the collection ratio was 31% or less (Comparative Examples 1 and 2).

In contrast, according to the method of the present disclosure, by setting the ratio of the flow rate of the passing collection liquid to the flow rate of the passing specimen at the time of cell capture or the flow velocity of the collection liquid in a specific range, and using a specific filter, for example, including a filter having a plurality of through holes, regardless of the viscosity of the collection liquid, collection of cells that were captured by the filter at a high collection ratio is realized. Furthermore, the method of the present disclosure may realize collection of cells at a high collection ratio, even with a collection liquid having a viscosity at which a sufficient collection ratio cannot be obtained in JP H10-201470A. That is, the method of the present disclosure is a technique having a different technical idea from those disclosed previously.

Also, the method of JP H10-201470A is a method for efficiently collecting white blood cells selectively from a mixture of white blood cells, platelets, and red blood cells for hematopoietic stem cells transplantation or the like, and JP H10-201470A discloses, as a preferred example, a means having a large surface area per volume, such as nonwoven fabric, as a means for capturing cells (white blood cells). In contrast, the method of the present disclosure is a technique that may be suitably used to collect rare cells captured by a filter having a plurality of through holes, for analysis, diagnosis, and the like. That is, JP H10-201470A and the method of the present disclosure have completely different purposes. Also, nonwoven fabric used in H10-201470A, and the filter having a plurality of through holes used in the present disclosure have different mechanisms with which cells are captured and different states in which cells are captured, and the method of the present disclosure and JP 1110-201470A have completely different technical ideas.

"Flow rate of passing liquid" in the present disclosure refers to the amount (volume) of liquid that flows per unit of time. In one or more embodiments, an example of the flow rate of passing liquid is the amount or volume of liquid that passes through the filter per unit of time.

"Flow rate per opening area of the filter" in the present disclosure refers to the velocity of liquid passing through opening portions or holes of the filter. In one or more embodiments, the flow velocity per opening area may be calculated by dividing the flow rate of passing liquid by the total area of the opening portions (holes).

Method for Collecting Cells

In one aspect, the present disclosure relates to a method by which cells captured by a filter having a plurality of through holes are collected from the filter (the collection method of the present disclosure). In one aspect, the collection method of the present disclosure includes passing a collection liquid through the filter on which cells are captured, in a direction that is reverse of a direction in which a specimen for capturing cells passes through the filter such that a ratio between a flow rate of the passing collection liquid and a flow rate of a passing specimen ([flow rate of collection liquid]/[flow rate of specimen]) is about 25 or more, and collecting a collection liquid remaining on the filter. Also, in one aspect, the collection method of the present disclosure includes passing the collection liquid through the filter on which cells are captured, in the direction that is reverse of the direction in which the specimen for capturing cells passes through the filter at a flow velocity of about 1 mm/sec or more per opening area, and collecting the collection liquid remaining on the filter.

According to the present disclosure, in one or more embodiments, it is possible to collect cells captured by the filter at a high collection ratio. According to the present disclosure, in one or more embodiments, it is possible to collect cells captured by the filter at a high collection ratio while suppressing damage to cells. Also, according to the present disclosure, in one or more embodiments, it is possible to collect cells with a small amount of the collection liquid, for example, at a level at which the collection liquid may be accommodated in a microtube.

The collection method of the present disclosure includes passing a collection liquid through the filter having a plurality of through holes in which cells are captured, in a direction that is reverse of the direction in which a specimen for capturing the cells passes through the filter. In one or more embodiments, the collection liquid may be passed by passing the collection liquid such that a ratio between the flow rate of the passing collection liquid and the flow rate of the passing specimen ([flow rate of collection liquid]/[flow rate of specimen]) is about 25 or more, or by passing the collection liquid at a flow velocity of about 1 mm/sec or more per opening area. By reversely feeding the collection liquid to the filter having the plurality of through holes under the above-described liquid passing conditions, in one or more embodiments, it is possible to collect cells captured by the filter at a high collection ratio while suppressing damage to cells. In the collection method of the present disclosure, "passing liquid in the reverse direction" or "backflow" also refers to as introducing the collection liquid from a filter surface that is opposite to a filter surface into which the specimen is introduced in order to capture cells, or letting the collection liquid flow from the side (e.g., downstream side) on which the specimen flows out at the time of passing the specimen toward the side (e.g., upstream side) on which the specimen flows in.

In one or more embodiments, the ratio between the flow rate of the passing collection liquid and the flow rate of the passing specimen ([flow rate of collection liquid]/[flow rate of specimen)] is about 25 or more, and from the viewpoint of increasing the ratio of collecting cells from the filter, the ratio is 100 or more, 150 or more, 200 or more, 300 or more, or 400 or more. From the viewpoint of suppressing damage to cells, the ratio is about 100,000 or less, 50,000 or less, or 25,000 or less. Also, from the viewpoint of further increasing the cell collection ratio, the ratio is about 1,000 or more, 1,200 or more, 1,500 or more, 2,000 or more, 2,200 or more, or 4,000 or more, and from a similar point, the ratio is about 15,000 or less, 12,000 or less, or 10,000 or less.

From the viewpoint of increasing the ratio of collecting cells from the filter, in one or more embodiments, the flow rate of the collection liquid is about 25 ml/min or more, 50 ml/min or more, 100 ml/min or more, 110 ml/min or more, or 120 ml/min or more. From the viewpoint of suppressing damage to cells, the flow rate is about 100,000 ml/min or less, 50,000 ml/min or less, or 10,000 ml/min or less. Also, from the viewpoint of further increasing the cell collection ratio, the flow rate is about 300 ml/min or more, 500 ml/min or more, or 550 ml/min or more, and from a similar point, the flow rate is about 7,000 ml/min or less, 6,000 ml/min or less, 5,000 ml/min or less, 4,000 ml/min or less, 3,000 ml/min or less, 2,000 ml/min or less, or 1,000 ml/min or less.

In one or more embodiments, from the viewpoint of causing turbulent flow on a filter surface that is opposite to the filter surface into which the specimen is introduced in order to capture cells, and increasing the ratio of collecting cells from the filter, the flow velocity of the collection liquid is about 1 mm/sec or more, 5 mm/sec or more, 10 mm/sec or more, 15 mm/sec or more, 20 mm/sec or more, 25 mm/sec or more, 30 mm/sec or more, or 35 mm/sec or more per opening area. From the viewpoint of suppressing damage to cells, the flow velocity is about 100,000 mm/sec or less, 50,000 mm/sec or less, or 30,000 mm/sec or less, 10,000 mm/sec or less, or 5,000 mm/sec or less. From the viewpoint of further increasing the cell collection ratio, the flow velocity is about 100 mm/sec or more, 150 mm/sec or more, or 160 mm/sec or more, and from a similar point, the flow velocity is 4,000 mm/sec or less, 3,500 mm/sec or less, 3,000 mm/sec or less, 2,000 mm/sec or less, or 1,500 mm/sec or less.

In one or more embodiments, the ratio between the amount of passing collection liquid and the amount of the passing specimen ([volume of collection liquid]/[volume of specimen that passes through filter]) is less than about 0.6, and from the viewpoint of increasing the ratio of collecting cells from the filter, the ratio is about 0.001 or more, 0.002 or more, 0.003 or more, 0.004 or more, or 0.005 or more. From the viewpoint of easily analyzing the collected cells, the ratio is less than about 0.6, 0.5 or less, or 0.4 or less. Also, from the viewpoint of further increasing the cell collection ratio, the ratio is about 0.006 or more, 0.007 or more, 0.008 or more, 0.009 or more, or 0.01 or more, and from a similar point, the ratio is about 0.3 or less, 0.2 or less, or 0.1 or less.

Pressure of the passing collection liquid is about 30 kPa or more and 150 kPa or less. From the viewpoint of increasing the ratio of collecting rare cells from the filter, in one or more embodiments, the pressure of the passing collection liquid is about 35 kPa or more, 40 kPa or more, 45 kPa or more, 50 kPa or more, or 55 kPa or more, and from a similar point, the pressure is about 130 kPa or less or 120 kPa or less.

In one or more embodiments, examples of the collection liquid include phosphate-buffered saline (PBS), PBS-BSA (for example, 0.2%), PBS-EDTA (for example, 1 mg/ml), and buffer solutions, isotonic solutions, and aqueous solvents such as water. In one or more embodiments, examples of the buffer solutions include Tris buffer solutions such as a Tris-HCl buffer solution, phosphate buffer solutions, HEPES buffer solutions, and citrate-phosphate buffer solutions. Also, examples of the isotonic solutions include physiological saline, a sucrose isotonic solution, a glucose isotonic solution, and a mannose isotonic solution.

In the collection method of the present disclosure, the viscosity of the collection liquid is not limited to a specific range defined in JP H10-201470A, and may be a viscosity in another range. There is no particular limitation on the viscosity of the collection liquid, and from the viewpoint of further increasing the cell collection ratio, in one or more embodiments, the viscosity at 25° C. is less than about 5 mPa·s, and the viscosity at 25° C. is about 0.5 mPa·s or more.

In one or more embodiments, the collection liquid may be passed through the filter using the above-described liquid passing pressure or a driving force with which the collection liquid may be passed through so as to satisfy the flow rate. In one or more embodiments, the collection liquid is introduced with (i) a method in which pressure is applied in the outlet direction of the flow channel, for example, on the side on which the specimen flows out (e.g. the downstream side), (ii) a method in which pressure is reduced in the inlet direction of the flow channel, for example on the side on which the specimen flows in (e.g., the upstream side), (iii) a method in which a syringe pump, a tube pump (also referred to as "roller pump" or "peristaltic pump"), or a plunger pump is used, (iv) a method in which a mechanical drive is utilized, or (v) the like.

According to the collection method of the present disclosure, in one or more embodiments, it is possible to collect cells from the filter with a small amount of the collection liquid at a high collection ratio. In one or more embodiments, the amount of the passing collection liquid is about 10 ml or less, 8 ml or less, 6 ml or less, 5 ml or less, 4 ml or less, 2 ml or less, or 1 ml or less, and 0.05 ml or more, 0.1 ml or more, or 0.2 ml or more.

In one or more embodiments, the collection method of the present disclosure may include passing the specimen containing cells through the filter. Rare cells that will be included in the specimen may be captured by the filter by passing the specimen through the filter.

From the viewpoint of increasing the cell capture ratio, in one or more embodiments, the flow rate of the passing specimen is about 0.01 ml/min or more, 0.05 ml/min or more, or 0.1 ml/min or more, and from a similar point, the flow rate is 100 ml/min or less, 50 ml/min or less, 25 ml/min or less, or 10 ml/min or less.

From the viewpoint of increasing the cell capture ratio, in one or more embodiments, the flow velocity of the specimen is about 0.01 mm/sec or more, 0.05 mm/sec or more, or 0.1 mm/sec or more per opening area, and from a similar point, the flow velocity is about 100 mm/sec or less, 50 mm/sec or less, 25 mm/sec or less, 10 mm/sec or less, 5 mm/sec or less, or 2 mm/sec or less.

The amount of the passing specimen or the amount of a blood specimen that passes through the filter is about 0.07 ml or more, 0.25 ml or more, 0.5 ml or more, 1 ml or more, an amount larger than about 1 ml, 2 ml or more, 3 ml or more, or 4 ml or more, with respect to a filtering area of 5 $mm^2$ to 10,000 $mm^2$, for example. Also, in one or more embodiments, from the viewpoint of maintaining the rare cell capture ratio, the amount of the passing specimen is about 6 L or less, 4 L or less, 2 L or less, 400 mL or less, 200 mL or less, 100 mL or less, 80 mL or less, 50 mL or less, 30 mL or less, 25 mL or less, 12 mL or less, 11 mL or less, 10 mL or less, 9 mL or less, or 8 mL or less, with respect to a filtering area of 5 $mm^2$ to 10,000 $mm^2$. Alternatively, in one or more embodiments, from the viewpoint of treating a large amount of the sample at once, capturing cells that tend to deform, and maintaining the rare cell capture ratio, the capacity of the filter is more than about 0.2 ml and less than about 130 ml or about 130 ml or less with respect to a filtering area of 15 $mm^2$ to 200 $mm^2$, and from a similar viewpoint, the capacity is about 0.8 ml to about 90 ml, about 0.8 ml to about 60 ml, about 2 ml to about 50 ml, or about 2 ml to about 40 ml.

From the viewpoint of increasing the cell capture ratio, in one or more embodiments, a pressure ($\Delta P1$) of the passing specimen is about 0.1 kPa or more or 0.2 kPa or more, and 2.6 kPa or less, 1.5 kPa or less, 1.3 kPa or less, 1.0 kPa, or 0.5 kPa or less. "Pressure of a passing specimen" in the present disclosure refers to a "difference in pressure of the whole system from an inlet of the system to its outlet", and for example, refers to a "difference in pressure of a system that extends from a tank in which the specimen is disposed to a waste liquid tank and includes a flow channel extending from the tank to the waste liquid tank". Thus, a pressure that is greater than or equal to the above-described pressure may be used depending on the structure of the flow channel. The pressure of a passing liquid (a difference in pressure of the system) may be measured using a commercially available pressure gauge with a known method, or may be calculated based on a relationship between the flow rate and the structure of the flow channel.

The filter used in the collection method of the present disclosure is a filter having a plurality of through holes. Because cells are captured by the filter having through holes, compared to nonwoven fabric, in one or more embodiments, it is possible to collect cells from the filter with a small amount of the collection liquid at a high collection ratio while reducing damage to cells. In one or more embodiments, an example of the filter is a slit-shaped filter having a plurality of through holes. In one or more embodiments, examples of the shape of the through holes include a rounded rectangle and an ellipse.

In one or more embodiments, an example of the filter used in the collection method of the present disclosure is a filter that may capture rare cells in a specimen. A filter that may be used in the labeling method of the present disclosure may be used as the filter.

Rare cells are separated from the filter by passing, to the filter through which the specimen has passed, the collection liquid in the direction that is reverse of the direction in which the specimen passed though the filter, and the collection liquid containing the separated rare cells is present on the filter. In one or more embodiments, the collection method of the present disclosure may include collecting the collection liquid that is present on the filter after the collection liquid passed through the filter. In one or more embodiments, the collection liquid may be collected using a pipette or the like. Also, during this collection, the collection liquid may or may not be stirred.

In one or more embodiments, the collection method of the present disclosure may include performing, at the filter, treatment on the cells captured by the filter. In one or more embodiments, examples of the treatment include fixation treatment, cell membrane permeation treatment, and staining treatment.

Method for Analyzing Rare Cells

As another aspect, the present disclosure relates to a method for analyzing rare cells in a blood specimen (the analysis method of the present disclosure), the method including collecting rare cells with the collection method of the present disclosure and observing dynamics of these cells or analyzing these cells with a method including activity measurement. According to the analysis method of the present disclosure, rare cells are collected with the collection method of the present disclosure, and thus the rare cells may be collected at a high collection ratio. Thus, according to the analysis method of the present disclosure, it is possible to highly precisely measure or analyze rare cells.

Cell Collection Apparatus

As another aspect, the present disclosure relates to a cell collection apparatus. According to the cell collection apparatus of the present disclosure, it is possible to collect cells with the collection method of the present disclosure at a high collection ratio. In one or more embodiments, the cell collection apparatus of the present disclosure is capable of collecting cells captured by a filter from the filter, and capturing cells using a filter, for example.

As one aspect, the cell collection apparatus of the present disclosure includes a separation portion provided with a filter having a plurality of through holes for capturing cells and a holding portion that holds the filter, at least one introduction flow channel for introducing a specimen containing cells into the separation portion, at least one liquid feeding means for supplying the specimen to the separation portion through the introduction flow channel, an ejection flow channel for ejecting the specimen that has passed through the separation portion to the outside, a container for accommodating a collection liquid for collecting cells captured in the separation portion, a reverse liquid feeding means for supplying the collection liquid from the container to the separation portion through the flow channel, and a control unit that controls the reverse liquid feeding means in order to collect cells with the cell collection method of the present disclosure. In one or more embodiments, the control unit controls the reverse liquid feeding means such that a ratio between a flow rate of the passing collection liquid and a flow rate of the passing specimen ([flow rate of collection liquid]/[flow rate of specimen]) is 25 or more, and/or the flow velocity of the collection liquid is 1 mm/sec or more per opening area.

In one or more embodiments, the separation portion includes at least a filter, and is detachably attached to the introduction flow channel and the ejection flow channel. In one or more embodiments, an example of the filter is the above-described filter.

In one or more embodiments, examples of the liquid feeding means and the reverse liquid feeding means include a pressurizing means, a pressure reducing means, a syringe pump, a tube pump (also referred to as "roller pump" or "peristaltic pump"), a plunger pump, and a mechanical drive.

In one or more embodiments, the liquid feeding means may be capable of introducing a treatment liquid for treating cells in a specimen into the separation portion through the introduction flow channel. In one or more embodiments, an example of the treatment liquid includes a treatment liquid used in fixation treatment, cell membrane permeation treatment, staining treatment, or the like. In one or more embodiments, the cell collection apparatus of the present disclosure may include a container for accommodating the treatment liquid for treating cells in the specimen.

In one or more embodiments, the control unit may record the filter used to capture cells, filtering conditions, and the like. In one or more embodiments, the control unit may be realized by a processor provided in a computer of the collection apparatus executing a predetermined program.

In one or more embodiments, the cell collection apparatus of the present disclosure includes a collection means for collecting the collection liquid supplied to the separation portion. In one or more embodiments, an example of the collection means is a nozzle mechanism. Cells may be collected by suctioning the collection liquid staying in the upper portion of the filter, with a nozzle, a pipette, or the like.

As another aspect, the cell collection apparatus of the present disclosure includes a control program with which cells may be collected with the collection method of the present disclosure.

Cell Collection System

As another aspect, the present disclosure relates to a cell collection system. According to the cell collection system of the present disclosure, it is possible to collect cells at a high collection ratio with the collection method of the present disclosure. In one or more embodiments, the cell collection system of the present disclosure is capable of collecting cells captured by a filter from the filter and capturing cells using a filter, for example.

In one or more embodiments, the cell collection system of the present disclosure includes a filter unit provided with a filter having a plurality of through holes for capturing cells and a holding portion that holds the filter, a separation unit provided with a flow channel portion in which the filter unit may be disposed and a liquid feeding means capable of passing a specimen containing cells to the filter through the flow channel portion, a collection unit provided with a flow channel portion in which a filter unit may be disposed and a reverse liquid feeding means capable of passing a collection liquid to the filter through the flow channel portion in a direction that is reverse of a direction in which the specimen passes through the separation unit, and a control unit that controls the reverse liquid feeding means for collecting cells with the cell collection method of the present disclosure. In one or more embodiments, the control unit controls the liquid feeding means of the separation unit and the liquid feeding means of the collection unit such that a ratio between a flow rate of the passing collection liquid and a flow rate of the passing specimen ([flow rate of collection liquid]/[flow rate of specimen]) is 2 about 5 or more, and/or the flow velocity of the collection liquid is 1 mm/sec or more per opening area. In one or more embodiments, the filter units are detachable from the flow channel portions of the separation unit and the collection unit. According to cell collection system of the present disclosure, in one or more embodiments, after cells are captured in the separation unit, the filter unit is moved into the collection unit, and the cells captured by the filter may be collected in the collection unit.

In one or more embodiments, the cell collection system of the present disclosure includes a separation portion provided with a filter having a plurality of through holes for capturing cells and a holding portion that holds the filter, at least one introduction flow channel for introducing a specimen containing cells into the separation portion, at least one liquid feeding means for supplying the specimen to the separation portion through the introduction flow channel, an ejection flow channel for ejecting the specimen that has passed through the separation portion to the outside, a container for accommodating a collection liquid for collecting cells captured in the separation portion, a reverse liquid feeding means for supplying the collection liquid from the container to the separation portion through the ejection flow channel, and a control unit that controls the reverse liquid feeding means in order to collect cells with the cell collection method of the present disclosure. In one or more embodiments, the control unit controls the reverse liquid feeding means such that a ratio between a flow rate of the passing collection liquid and a flow rate of the passing specimen ([flow rate of collection liquid]/[flow rate of specimen]) is 25 or more, and/or the flow velocity of the collection liquid is 1 mm/sec or more per opening area.

Figure 4:
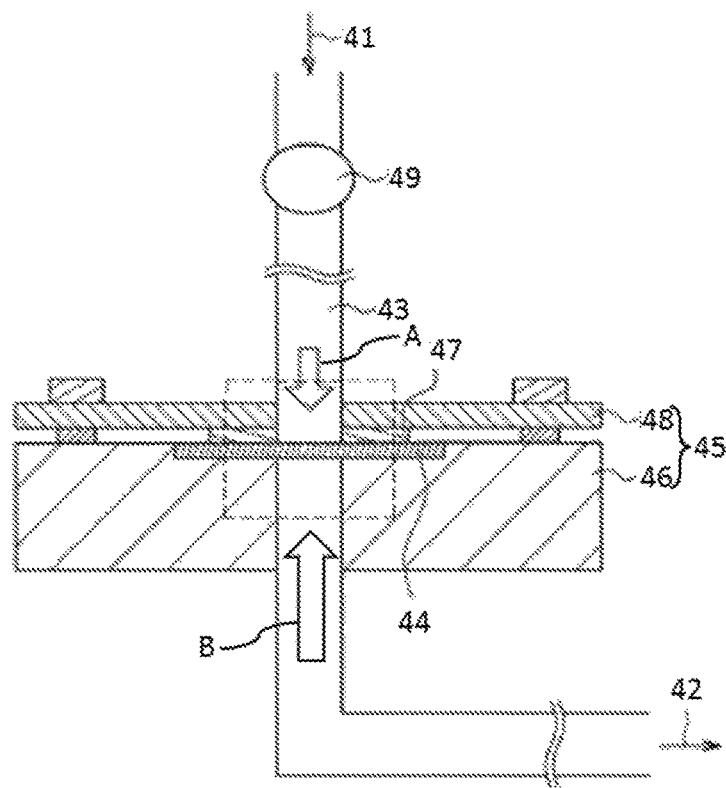
FIG. 4 shows one example of a rare cell capture collection apparatus used in Example 11.

FIG. 4 shows one example of a rare cell capture and collection apparatus that may be utilized in the collection method or the analysis method of the present disclosure. The rare cell capture and collection apparatus shown in FIG. 4 includes a supply port 41 for supplying a specimen, a washing liquid, a staining liquid, and the like to a filter, an ejection port 42, a flow channel 43 that connects the supply port 41 and the ejection port 42, and a separation portion disposed at a position corresponding to a portion of the flow channel 43. The separation portion includes a filter 44 and a filter holder 45 that holds the filter 44. The filter holder 45 is constituted by a support portion (base) 46 in which the filter 44 may be installed, an O-ring 47 to which the filter 44 is fixed, and a cover 48. The filter 44 is installed in the support portion 46, the O-ring 47 and the cover 48 are placed on an upper surface of the filter 44, the filter 44 is fixed, and thereby, a separation portion (filter device) provided with the filter having holes is formed. The flow channel 43 that connects the supply port 41 and the separation portion and the separation portion and the ejection port 42 is formed by connecting Safeed (trademark) tubes (produced by TERUMO CORPORATION) to both ends of the separation portion. The flow channel 43 that connects the supply port 41 and the separation portion may be provided with a connection portion (not shown) and a three-way stopcock valve (not shown) that may switch liquids, in the upper portion of the separation portion. Also, the flow channel 43 that connects the supply port 41 and the separation portion may be provided with a pressurizing means 49 (as the mechanism capable of feeding liquid at a constant pressure or a mechanism capable of feeding liquid at a constant flow rate) such that a constant pressure is applied to filtering, or liquid may be drawn by a syringe pump and fed through the flow channel 43 such that pressure applied to filtering does not reach a predetermined value or more.

Figure 5:
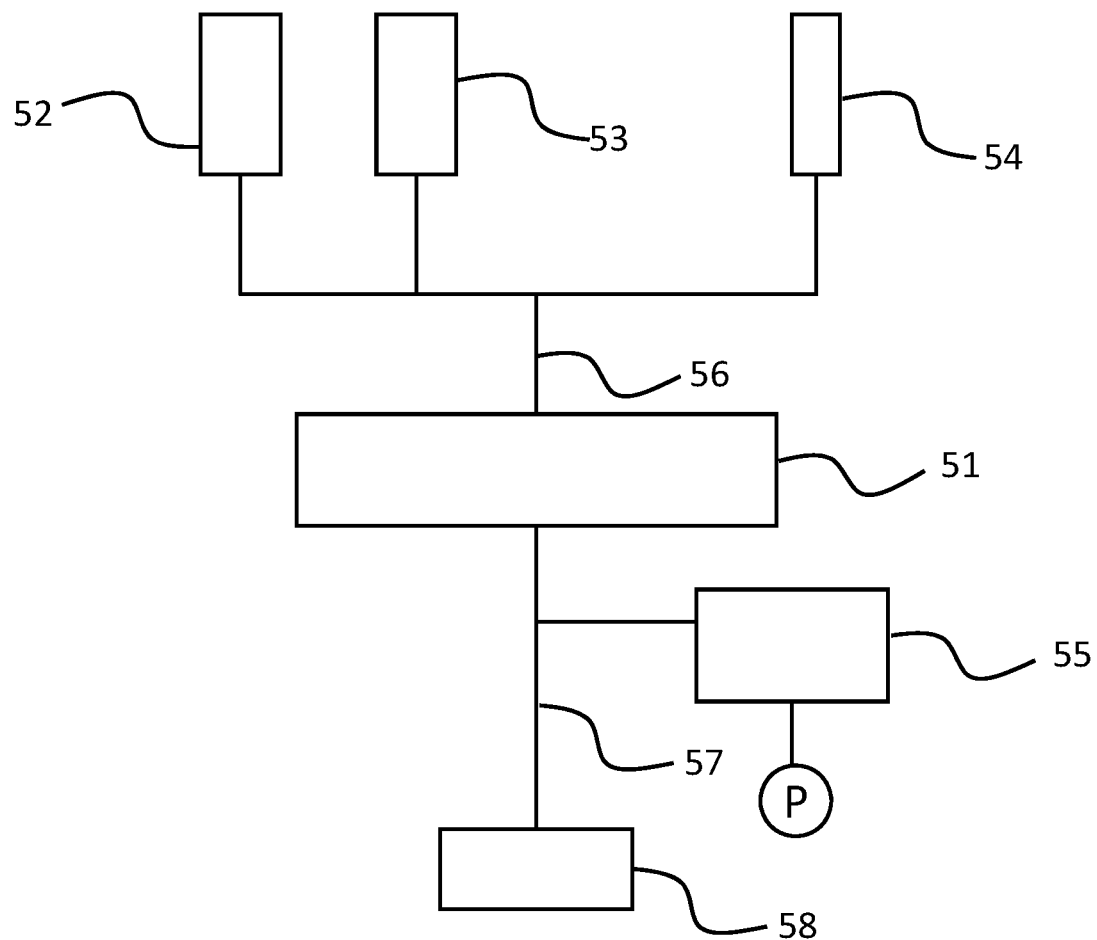
FIG. 5 shows one example of a configuration of a cell capture collection apparatus that may be used in a cell collection method of the present disclosure.

FIG. 5 shows another example of a rare cell capture and collection apparatus that may be utilized in the collection method or the analysis method of the present disclosure. The rare cell capture and collection apparatus shown in FIG. 5 includes an introduction flow channel 56 for introducing a specimen in a container 52 into a separation portion 51, a separation portion 51 provided with a filter, a container 55 that accommodates a collection liquid, and an ejection flow channel 57 for ejecting a waste liquid ejected from the separation portion 51. The container 55 that accommodates the collection liquid is connected to the ejection flow channel 57 through a flow channel such that the collection liquid may be reversely fed to the separation portion 51 through the ejection flow channel 57. A liquid feeding means for reversely feeding the collection liquid to the separation portion 51, such as a pump, is connected to the container 55. In addition to the container 52 that accommodates a specimen, for example, a container 13 that accommodates a washing liquid and a container 54 that accommodates a treatment liquid for treating cells in the specimen may be connected to the introduction flow channel 56 through the flow channel. A container 58 for collecting the waste liquid may be disposed at one end of the ejection flow channel 57.

There is no particular limitation on "cells" in the present disclosure, and examples of the cells include human cells or cells of an animal other than a human.

"Rare cells" in the present disclosure refer to cells other than blood cells (red blood cells, white blood cells, and platelets) that may be included in human blood or the blood of an animal other than a human. In one or more embodiments, examples of the rare cells include tumor cells and cancer cells. In general, tumor cells and cancer cells that circulate in blood are referred to as CTCs. As the number of rare cells in blood, depending on the specimen though, 10 ml of blood contains several to dozens of rare cells, and contains up to hundreds to thousands of rare cells in some cases. In one or more embodiments, "rare cells" are cells selected from the group consisting of cancer cells, circulatory tumor cells, vascular endothelial cells, vascular endothelial progenitor cells, cancer stem cells, epithelial cells, hematopoietic stem cells, mesenchymal stem cells, fetal cells, stem cells, and combinations thereof.

In not particularly limited one or more embodiments, examples of the rare cells include human colon cancer cells, human stomach cancer cells, human large bowel cancer cells, human lung cancer cells, human lung cancer cells, human lung cancer cells, human lung cancer cells, and human lung cancer cells.

An example of "specimen" in the present disclosure is a sample that will contain cells that will be applied to the collection method of the present disclosure. In one or more embodiments, an example of the specimen is a blood specimen. In one or more embodiments, the blood specimen is a sample containing components constituting blood, and in not particularly limited one or more embodiments, examples thereof include blood, blood origins containing blood cell components, body fluid and urine in which blood or blood origins are mixed in, and a sample prepared from these. An example of blood is blood collected from an organism, and an example of the organism includes a human and an animal (for example, a mammal) other than a human. Examples of the blood origins containing blood cell components include samples that are separated or prepared from blood and contain blood cell components, and dilutions/concentrates thereof, such as blood cell fractions from which blood plasma is removed, blood cell concentrates, lyophilizates of blood or blood cells, samples obtained by subjecting whole blood to hemolysis treatment and removing red blood cell components, hemolyzed samples, centrifuged blood, spontaneously sedimented blood, washed blood cells, and a specific fraction. Among these, in non-limited one or more embodiments, from the viewpoint of easy and quick treatment and suppressing damage to rare cells in blood, blood or a specimen derived from blood containing blood cell components is preferable as the sample containing the blood.

The present disclosure relates to one or more embodiments below.

[C1] A method for collecting cells captured by a filter having a plurality of through holes from the filter, the method including:
  passing a collection liquid through the filter on which cells are captured, in a direction that is reverse of a direction in which a specimen for capturing the cells passes through the filter,
  in which the collection liquid is passed through the filter such that a ratio between a flow rate of the passing collection liquid and a flow rate of the passing specimen ([flow rate of collection liquid]/[flow rate of specimen]) is about 25 or more.

[C2] A method for collecting cells captured by a filter having a plurality of through holes from the filter, the method including:
  passing a collection liquid through the filter on which cells are captured, in a direction that is reverse of a direction in which a specimen for capturing the cells passes through the filter, at a flow velocity of 1 mm/sec or more per opening area of the filter.

[C3] The collection method according to [C1], including passing the collection liquid through the filter at a flow velocity of 1 mm/sec or more per opening area of the filter.

[C4] The collection method according to any of [C1] to [C3], including letting the filter capture the cells by passing the specimen containing the cells through the filter at a flow velocity of 0.01 mm/sec to 100 mm/sec per opening area.

[C5] The collection method according to any of [C1] to [C4], in which the filter is a filter capable of capturing rare cells.

[C6] The collection method according to any of [C1] to [C5], in which a material of the filter is selected from the group consisting of nickel, SUS, gold, silver, copper, aluminum, tungsten, and chromium.

[C7] The collection method according to any of [C1] to [C7], in which the cells are rare cells.

[C8] A method for analyzing rare cells in a blood specimen, the method including collecting rare cells with the collection method according to any of [C1] to [C7], and observing dynamics of these cells or analyzing these cells with a method including activity measurement.

[C9] A cell collection apparatus including:
  a separation portion provided with a filter having a plurality of through holes for capturing cells and a holding portion that holds the filter;
  at least one introduction flow channel for introducing a specimen containing cells into the separation portion;
  at least one liquid feeding means for supplying the specimen to the separation portion through the introduction flow channel;
  an ejection flow channel for ejecting the specimen that passed the separation portion to the outside;
  a container for accommodating a collection liquid for collecting cells captured in the separation portion;

a reverse liquid feeding means for supplying the collection liquid from the container to the separation portion through the ejection flow channel; and a control unit that controls the reverse liquid feeding means such that a ratio between a flow rate of the passing collection liquid and a flow rate of the passing specimen ([flow rate of collection liquid]/[flow rate of specimen]) is 25 or more.

[C10] A cell collection apparatus including:

a separation portion provided with a filter having a plurality of through holes for capturing cells and a holding portion that holds the filter;

at least one introduction flow channel for introducing a specimen containing cells into the separation portion;

at least one liquid feeding means for supplying the specimen to the separation portion through the introduction flow channel;

an ejection flow channel for ejecting the specimen that passed the separation portion to the outside;

a container for accommodating a collection liquid for collecting cells captured in the separation portion;

a reverse liquid feeding means for supplying the collection liquid from the container to the separation portion through the ejection flow channel; and a control unit that controls the reverse liquid feeding means such that the collection liquid is passed at a flow velocity of 1 mm/sec or more per opening area.

[C11] A cell collection apparatus provided with a program for controlling the collection method according to any of [C1] to [C7].

[C12] The cell collection apparatus according to [C9] or [C10] provided with a program for controlling the collection method according to any of [C1] to [C7].

[C13] The cell collection apparatus according to any of [C9] to [C12], including a collection means for collecting a collection liquid supplied to the separation portion.

[C14] A cell collection system including:

a filter unit provided with a filter having a plurality of through holes for capturing cells and a holding portion that holds the filter;

a separation unit provided with a flow channel portion in which the filter unit may be disposed and a liquid feeding means capable of passing a specimen containing cells through the filter through the flow channel portion;

a collection unit provided with a flow channel portion in which the filter unit may be disposed and a reverse liquid feeding means capable of passing a collection liquid through the filter through the flow channel portion in a direction that is reverse of a direction in which the specimen passes through the filter in the separation unit; and a control unit that controls the liquid feeding means of the separation unit and the liquid feeding means of the collection unit such that a ratio between a flow rate of the passing collection liquid and a flow rate of the passing specimen ([flow rate of collection liquid]/[flow rate of specimen]) is about 25 or more.

[C15] A cell collection system including:

a filter unit provided with a filter having a plurality of through holes for capturing cells and a holding portion that holds the filter;

a separation unit provided with a flow channel portion in which the filter unit may be disposed and a liquid feeding means capable of passing a specimen containing cells through the filter through the flow channel portion;

a collection unit provided with a flow channel portion in which the filter unit may be disposed and a reverse liquid feeding means capable of passing a collection liquid through the filter through the flow channel portion in a direction that is reverse of a direction in which the specimen passes through the filter in the separation unit; and a control unit that controls the liquid feeding means of the separation unit and the liquid feeding means of the collection unit such that the collection liquid is passed at a flow velocity of about 1 mm/sec or more per opening area.

EXAMPLES

Hereinafter, the present disclosure will be further described using Examples. However, the present disclosure is not to be interpreted as being limited to Examples below. A cell capture/labeling apparatus and a cell capture apparatus that will be described below may be configured by combining a plurality of units.

1. Confirmation of Magnetic Labeling Efficiency

Example 1

A cell capture/labeling apparatus shown in FIG. 1 was used to capture cells (white blood cells) and label the cells with magnetic particles, and the labeling efficiency was checked.

Cell Labeling Apparatus

A cell labeling apparatus shown in FIG. 1 was prepared. The cell labeling apparatus in FIG. 1 includes a device upper portion 3, a filter portion 5 including a filter 10, a device lower portion 4, and a liquid feeding mechanism (not shown) capable of feeding liquid in an arrow A direction and an arrow B direction. The filter 10 is disposed between the device upper portion 3 and the device lower portion 4, and is fixed by both-sided tapes 11 and 12. A filter including a plurality of through holes and having properties below was used as the filter 10.

Properties of Filter

Through hole short axial diameter: 6.5 µm, long axial diameter: 88 µm, area: 572 µm$^2$, shape: slit Pitch between centers of holes: 14 µm×100 µm (short axial diameter side×long axial diameter side)

Hole density: 714 holes/mm$^2$

Opening ratio: 41%

Membrane thickness: 5 µm

Material: nickel

Filtering area: 79 mm$^2$

Magnetic Particle Labeling

Cells (white blood cells) included in blood were labeled with magnetic particles using the cell labeling apparatus in FIG. 1 with the procedure of steps 1 to 8 below.

Step 1: 8 mL of blood containing rare cells and white blood cells was introduced into the cell labeling apparatus, blood was filtered through the filter and cells such as rare cells and white blood cells were captured by size selection (filtering flow rate: 100 µL/min, flow velocity: 0.144 mm/sec).

Step 2: an antibody liquid containing antibodies against CD45 and CD50 and an antibody liquid containing biotinylated antibodies that recognized the antibodies were supplied to the filter in this order and allowed to react with cells, and CD45 expressing cells and CD50 expressing cells (for example, white blood cells) were biotinylated. The antibody liquids stayed not only in the upper portion of the filter but also in the lower portion of the filter so as to be in contact with both surfaces of the filter.

Step 3: suspension containing neutravidin labeled magnetic particles was supplied to the upper surface of the filter, and a portion of the suspension was fed from the filter upper portion in the arrow A direction shown in FIG. 1 such that the lower surface of the suspension was located below the lower surface of the filter.

Step 4: the suspension was caused to flow backward from the lower portion of the filter in the arrow B direction shown in FIG. 1 (the flow rate of backflow: 10,000 µL/min, flow velocity: 14.441 mm/sec).

Step 5: the suspension in the upper portion of the filter was stirred by pipetting.

Step 6: the stirred suspension (liquid obtained by stirring cells and magnetic particles) in the upper portion of the filter was fed again in the arrow A direction shown in FIG. 1 (the flow rate: 250 µL/min).

Step 7: a washing liquid that did not contain magnetic particles was fed in the arrow A direction shown in FIG. 1. Accordingly, unreacted magnetic particles were removed.

Step 8: a collection liquid was fed from the lower portion of the filter in the arrow B direction shown in FIG. 1, the collection liquid that stayed in the upper portion of the filter was suctioned with a pipette, and the cells (the white blood cells that were labeled with magnetic particles and the rare cells were collected together with the collection liquid.

Evaluation of Labeling Efficiency

Figure 3:
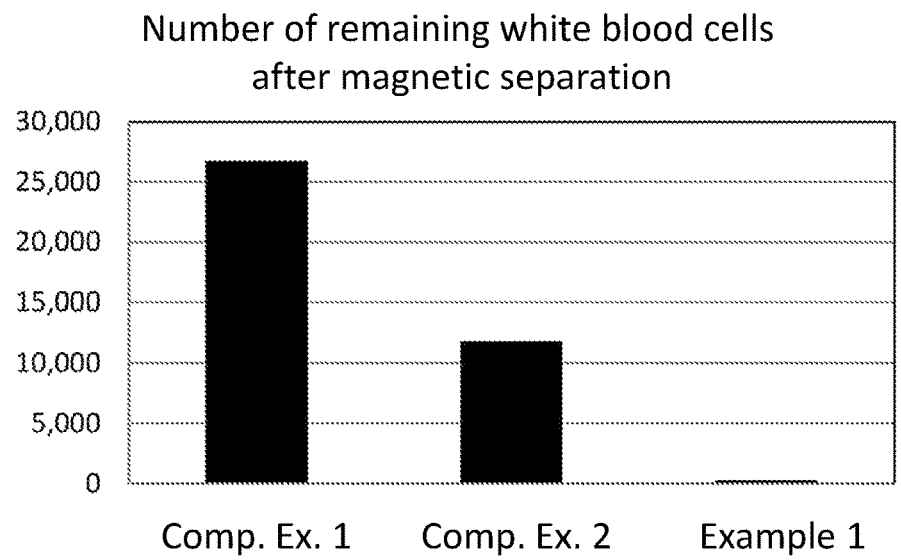
FIG. 3 is a graph showing one example of the number of white blood cells remaining (that were not captured magnetically) in Example 1, and Comparative Examples 1 and 2.

The cells that were collected in step 8 were magnetically separated using a neodymium magnet. The number of white blood cells that were collected and not captured by the magnet was counted. The results are shown in FIG. 3.

Comparative Example 1

An experiment was performed similarly to Example 1 except that steps 4 to 6 were not performed. The results are shown in FIG. 3.

Comparative Example 2

An experiment was performed similarly to Example 1 except that step 4 was not performed. The results are shown in FIG. 3.

As shown in FIG. 3, according to the method of Example 1, the number of remaining white blood cells, that is, the number of white blood cells that were not captured with the magnet through magnetic separation was reduced significantly. Thus, according to the method of Example 1, it may be said that white blood cells were magnetically labeled at the filter at a high labeling efficiency.

Example 2

Preparation of Sample

Biotinylated white blood cells labeled with fluorescence were prepared with procedures below.

First, whole blood was collected from a human using a vacuum blood collection tube (EDTA 2K).

Next, white blood cells were separated from the collected whole blood in accordance with the accompanying document of HetaSep (STEMCELL Inc.).

$1 \times 10^6$ white blood cells that were separated with HetaSep were reacted with a blocking liquid (obtained by dissolving a 10% goat serum, 0.000001% Avidin, 0.2% BSA in a Dulbecco's PBS (−)) at 23° C. for 10 minutes. The sample was centrifuged to remove a supernatant, and then resuspended using the Dulbecco's PBS (−). The sample was centrifuged again to remove a supernatant.

Next, a primary antibody reaction liquid was prepared by adding an anti-CD45 antibody and an anti-CD50 antibody to the Dulbecco's PBS (−) that was obtained by dissolving a 10% goat serum, 0.01% Biotin, and 0.2% BSA in accordance with the package insert. Cells (white blood cells) were suspended in the prepared primary antibody reaction liquid and reacted at 23° C. for 15 minutes. The sample was centrifuged to remove a supernatant, and then resuspended using the Dulbecco's PBS (−). Thereafter, the step of centrifugation to remove a supernatant was performed three times in total and cells were washed sufficiently.

A secondary antibody reaction liquid was prepared by adding Alexa594 labeled anti-mouse IgG(Fab) and biotinylated anti-mouse IgG(Fc) to a Dulbecco's PBS (−) that was obtained by dissolving 2 µg/ml Hoechst33342, a 10% goat serum, and 0.2% BSA in accordance with the package insert. The cells that were washed with the prepared secondary antibody reaction liquid were resuspended and reacted at 23° C. for 15 minutes. The sample was centrifuged to remove a supernatant, and then resuspended using the Dulbecco's PBS (−). The step of centrifugation to remove a supernatant was performed three times in total and cells (white blood cells) were washed sufficiently.

Accordingly, a sample containing biotinylated white blood cells labeled with fluorescence was prepared.

Capture Cells

Similarly to Example 1, the sample containing biotinylated white blood cells labeled with fluorescence ($1 \times 10^5$) was introduced into the cell labeling apparatus shown in FIG. 1 in an arrow 1 direction, and was filtered through the filter at a flow rate of 100 µL/min (the flow velocity: 0.144 mm/sec).

A filter including a plurality of through holes and having properties below was used as the filter 10.

Properties of Filter

Through hole short axial diameter: 6.5 µm, long axial diameter: 88 µm, area: 572 µm², shape: slit Pitch between centers of holes: 14 µm×100 µm (short axial diameter side×long axial diameter side)

Hole density: 714 holes/mm²

Opening ratio: 41%

Membrane thickness: 5 µm

Material: nickel

Filtering area: 28 mm².

Magnetic Particle Labeling

A solution obtained by dissolving 0.2% BSA in the Dulbecco PBS (−) was fed to the apparatus shown in FIG. 1, and the flow channel 8 was filled therewith. 200 µL of a magnetic particle liquid (suspension containing neutravidin labeled magnetic particles, the concentration of the solid content: 0.0125%) was added onto the upper surface of the filter 10, and a portion of the added magnetic particle liquid (100 µL) was fed and filtered such that the lower surface of the magnetic particle liquid is located below the lower surface of the filter 10. 200 µL of a solution obtained by dissolving 0.2% BSA in the Dulbecco PBS (−) was fed in the arrow B direction shown in FIG. 1 at a flow rate of 10000 µL/min using a backflow liquid feeding mechanism. The solution (the concentration of the solid content: 0.0062%) on the filter 10 was stirred with a pipette, and then reacted at 23° C. for 15 minutes. Next, 300 µL of the magnetic particle liquid containing white blood cells on the upper surface of the filter 10 was fed in the arrow A direction shown in FIG. 1 at a flow rate of 250 µL/min, and reacted at 23° C. for 15 minutes. Accordingly, white blood cells were magnetically labeled with magnetic particles.

Wash Magnetic Particles

Thereafter, 1000 µL of the Dulbecco PBS (−) obtained by dissolving 1 mg/mL EDTA was added to the upper surface of the filter 10, and then was fed in the arrow A direction shown in FIG. 1 at a flow rate of 1000 µL/min. This step was performed four times in total so as to wash off excess magnetic particles on the filter 10.

Collection of Cells

1000 µL of a solution obtained by dissolving 0.2% BSA in the Dulbecco PBS (−) was fed in the arrow B direction shown in FIG. 1 at a flow rate of 10000 µL/min using a backflow liquid feeding mechanism. Then, all of the 1100 µL of solution on the filter 10 was collected through pipette suction.

Evaluation of Labeling Efficiency

The collected suspension was magnetically separated, and the labeling efficiency was evaluated by determining white blood cells that were not magnetically separated (were not captured with a magnet) to be not magnetically labeled (or insufficiently labeled).

That is, the collected cells were magnetically separated using a neodymium magnet. The number of white blood cells that were collected without being captured by the magnet was counted.

Specifically, in the cells included in 1000 µL of the collected suspension, the number of cells that were Alexa594 and Hoechst33342 positive were counted using a fluorescence microscope (the number of white blood cells after magnetic separation (LEUK-a)).

On the other hand, white blood cells in 100 µL of the suspension that was not used in magnetic separation in the collected was counted using a hemocytometer (Moxi-Z), and the number of white blood cells in 1000 µL was calculated (the number of white blood cells before magnetic separation (LEUK-b)).

An unlabeled ratio was calculated with an equation below using the obtained number of white blood cells (LEUK-a and LEUK-b). The results are shown in Table 1 below.

[Unlabeled ratio]={1−([LEUK-b]−[LEUK-a]/[LEUK-b])}×100

Examples 3 to 5

An experiment was performed similarly to Example 2 except that a sample that was newly prepared with the same preparation method as Example 2 was used and the flow rate of the suspension of magnetic particles during backflow liquid feeding was set to flow rates in Table 1 below. The results are shown in Table 1 below.

Comparative Example 3

An experiment was performed similarly to Example 2 except that a sample was newly prepared with the same preparation method as Example 2 was used and backflow liquid feeding was not performed in magnetic particle labeling. That is, magnetic particle labeling was performed by feeding and filtering a portion (100 µL) of a magnetic particle liquid (200 µL) that was added to the upper surface of the filter, then stirring the solution on the filter with a pipette, and undergoing reaction at 23° C. for 30 minutes. The results are shown in Table 1 below.

TABLE 1

| | Backflow liquid feeding | | Number of white blood cells | | Unlabeled ratio | |
|---|---|---|---|---|---|---|
| | flow velocity (mm/sec) | flow rate (µL/min) | after separation (LEUK-a) | before separation (LEUK-b) | % | relative value |
| Ex. 2 | 14.441 | 10000 | 73 | 59000 | 0.12% | 7 |
| Ex. 3 | 1.444 | 1000 | 113 | 54000 | 0.21% | 12 |
| Ex. 4 | 0.144 | 100 | 213 | 48000 | 0.44% | 25 |
| Ex. 5 | 0.014 | 10 | 447 | 56000 | 0.80% | 45 |
| Comp. Ex. 3 | — | — | 743 | 42000 | 1.77% | 100 |

*relative value: relative value of remaining ratio in case where remaining ratio (%) of Comp. Ex. 3 is 100.

As shown in Table 1, the unlabeled ratio, that is, the ratio of white blood cells that were not magnetically labeled (or insufficiently labeled) was reduced to less than 1% by labeling cells with the methods of Examples 2 to 5. That is, according to the methods of Examples 2 to 5, white blood cells were magnetically labeled at the filter at a high labeling efficiency.

Example 6

An experiment was performed similarly to Example 2 except that a sample that was newly prepared with the same method as Example 2 was used and backflow liquid feeding was performed twice, 100 µL at a time, after a portion of the magnetic particle liquid was fed and filtered (the total feeding amount: 200 µL). The results are shown in Table 2 below.

Example 7

An experiment was performed similarly to Example 2 except that a sample that was newly prepared with the same method as Example 2 was used. The results are shown in Table 2 below.

TABLE 2

| | | Number of white blood cells | | |
|---|---|---|---|---|
| | Number of instances of backflow | after separation (LEUK-a) | before separation (LEUK-b) | Unlabeled ratio % |
| Example 6 | 2 | 130 | 26000 | 0.50% |
| Example 7 | 1 | 133 | 25000 | 0.53% |
| Comp. Ex. 3 | 0 | 743 | 42000 | 1.77% |

As shown in Table 2, in both cases of the methods of Examples 6 and 7, white blood cells were magnetically labeled at the filter at a high labeling efficiency. Also, it was found that a desired effect was obtained by performing backflow liquid feeding at least once after the magnetic particle liquid was fed and filtered.

It is conceivable that the reason why Example 7 and Example 2 that were performed under the same treatment conditions had different unlabeled ratios is a difference between specimens that were used, specifically, a difference in white blood cells that were included in the specimens. Although in the above-described Examples, labeling with magnetic particles was performed using a CD antigen that was expressed on the surface of white blood cells, it is known that expression of the CD antigen has a difference between specimens caused by inter-individual variation (in-dividual difference) or variation within an individual. It is conceivable that Example 7 and Example 2 had different unlabeled ratios due to this difference between specimens. With the method of the present disclosure, it was confirmed that a sufficient reproducibility of the labeling ratio was obtained when the same specimen was used.

Example 8

An experiment was performed similarly to Example 2 except that a sample that was newly prepared with the same preparation method as Example 2 was used. The results are shown in Table 3 below.

Example 9

An experiment was performed similarly to Example 8 except that a sample that was newly prepared with the same preparation method as Example 2 was used and stirring with a pipette was not performed. The results are shown in Table 3 below.

TABLE 3

| | Stirring with pipette | Number of white blood cells | | Unlabeled ratio % |
|---|---|---|---|---|
| | | after separation (LEUK-a) | before separation (LEUK-b) | |
| Example 8 | yes | 33 | 44000 | 0.08% |
| Example 9 | no | 110 | 25000 | 0.44% |

As shown in Table 3, with the methods of Examples 8 and 9, white blood cells were magnetically labeled at the filter at a high labeling efficiency. In particular, the magnetic label-ing efficiency was further increased through stirring with a pipette after backflow liquid feeding.

Comparative Example 4

An experiment was performed similarly to Example 8 except that a sample that was newly prepared with the same preparation method as Example 2 was used and a portion of the magnetic particle liquid was not fed before backflow liquid feeding (FIG. 2(b)). The results are shown in Table 4 below together with the results of Example 8.

TABLE 4

| | Feeding of magnetic particles to lower portion of filter | Number of white blood cells | | Unlabeled ratio | |
|---|---|---|---|---|---|
| | | after separation (LEUK-a) | before separation (LEUK-b) | % | relative value |
| Example 8 | yes | 33 | 44000 | 0.08% | 7 |
| Comp. Ex. 4 | no | 310 | 30000 | 1.03% | 100 |

*relative value: relative value of remaining ratio in case where remaining ratio (%) of Comp. Ex. 4 is 100.

As shown in Table 4, white blood cells that were captured by the filter were magnetically labeled at a high labeling efficiency by, before backflow liquid feeding, feeding and filtering a portion of the magnetic particle liquid that was added to the upper surface of the filter. That is, it was found that the labeling efficiency increased by causing backflow after both surfaces of the filter were immersed in the suspension.

2. Cell Capture and Collection Testing with Filter

Experiment Example 1

Rare cells in a blood specimen were collected using a rare cell capture apparatus shown in FIG. 4.

A filter having properties below was used as the filter. The filter having the properties below is capable of capturing SNU-1 and SW620.
Properties of Filter
Through hole short axial diameter: 6.5 µm, long axial diameter: 88 µm, area: 572 µm$^2$, shape: slit
Pitch between centers of holes (short axial diameter side× long axial diameter side): 14 µm×100 µm
Hole density: 714 holes/mm$^2$
Opening ratio: 41%
Membrane thickness: 5 µm
Material: nickel
Filtering area: 79 mm$^2$ A rare cell capture collection apparatus shown in FIG. 4 was constructed, the rare cell capture collection apparatus including the above-described filter and a liquid feeding unit including a backflow liquid feeding mechanism. An alumi-num member was used as a member support portion 46 that fixes the filter. Rare cells were captured through filtering with the filter and the captured cells were collected from the filter under the conditions shown in Table 5 below, using that rare cell capture collection apparatus. Specifically, an experiment was performed as follows.

First, cells were captured through filtering. 7.5 ml of a blood specimen containing SNU-1 cells that were stained with Celltracker green was passed at a constant pressure in the arrow A direction shown in FIG. 4 for approximately 30 minutes (ΔP1=0.75 kPa: filtering flow rate was 0.25 ml/min) (liquid may be passed at this low pressure utilizing a head pressure, the same pump as the above-described backflow liquid feeding mechanism, or a pump that is separate from the backflow feeding mechanism.). Accordingly, SNU-1 cells were captured at the filter. Next, after the filter was washed by passing 4 mL of PBS (−) twice, 900 µL of an ammonium chloride solution (ACS) was passed through the filter three times to cause hemolysis at room temperature for 10 minutes. The filter was washed by passing 4 mL of PBS (−), and liquid in the device was replaced. A flow channel that connected the supply port 41 and the separation portion was removed and was sealed with a cover glass, and then the number of SNU-1 cells that were captured by the filter was counted through microscopy.

After counting, the cover glass was removed, and an acrylic plate provided with wells for collection that was designed to correspond to the position and the size of the flow channel in the upper portion of the filter was set on the cover 48.

Thereafter, the cells that were captured by the filter were collected. 1 ml of PBS (−) (a collection liquid, viscosity: 0.95 mPa·s) was passed through the filter using the backflow liquid feeding mechanism in a direction (in the arrow B direction shown in FIG. 4) that was reverse of the liquid passing direction in which the above-described cells were captured (the flow rate was 120 ml/min). The collection liquid that stayed in the upper portion of the filter was suctioned with a pipette, and the total amount thereof was collected. The number of SNU-1 cells in the collected liquid was counted through microscopy. The collection ratio was obtained by dividing the number of SNU-1s in the collected liquid by the number of SNU-1 cells that were captured by the filter. The results are shown in Table 5 below.

Experiment Example 2

Cells were captured and collected similarly to Experiment Example 1 except that the amount of the collection liquid was 0.25 ml and the flow rate was 6,000 ml/min. The results are shown in Table 5 below.

Experiment Example 3

Cells were captured and collected similarly to Experiment Example 1 except that the amount of the collection liquid was 0.5 ml and the flow rate was 6,000 ml/min. The results are shown in Table 5 below.

Experiment Example 4

Cells were captured and collected similarly to Experiment Example 1 except that the flow rate of the collection liquid was 6,000 ml/min. The results are shown in Table 5 below.

Experiment Example 5

Cells were captured and collected similarly to Experiment Example 1 except that the amount of the collection liquid was 0.25 ml and the flow rate was 600 ml/min. The results are shown in Table 5 below.

Experiment Example 6

Cells were captured and collected similarly to Experiment Example 1 except that the flow rate of the collection liquid was 600 ml/min. The results are shown in Table 5 below.

Experiment Example 7

Cells were captured and collected similarly to Experiment Example 1 except that the filtering area was 20 mm$^2$, ΔP1 was 0.4 kPa (liquid was fed for approximately 60 to 120 minutes), and the flow rate of the collection liquid was 600 ml/min. The results are shown in Table 5 below.

Experiment Example 8

Cells were captured and collected similarly to Experiment Example 1 except that the filtering area was 20 mm$^2$, and ΔP1 was 0.4 kPa (liquid was fed for approximately 60 to 120 minutes). The results are shown in Table 5 below.

Experiment Example 9

Cells were captured and collected similarly to Experiment Example 1 except that the filtering area was 20 mm$^2$, ΔP1 was 0.4 kPa (liquid was fed for approximately 30 minutes) and the amount of a blood specimen was 4 ml. The results are shown in Table 5 below.

Experiment Example 10

Cells were captured and collected similarly to Experiment Example 1 except that the filtering area was 20 mm$^2$, ΔP1 was 0.75 kPa (liquid was fed for approximately 10 minutes), and the amount of a blood specimen was 4 ml. The results are shown in Table 5 below.

Experiment Example 11

First, cells were captured through filtering with a filter. With the same method as Experiment Example 1, 2 ml of the blood specimen containing SW620 cells stained with Cell-tracker green was passed at a constant pressure in the arrow A direction shown in FIG. 4 for approximately 8 minutes (ΔP1=0.4 kPa: filtering flow rate=0.25 ml/min). Accordingly, SW620 cells were captured at the filter below. Similarly to Experiment Example 1, hemolysis treatment was performed, the filter was washed with PBS (−), and then fixation treatment and cell membrane permeation treatment were performed at the filter. The fixation treatment was performed by passing 4% paraformamide:PFA (PBS (−) solution), filling the vicinity of the filter therewith, and then causing reaction at room temperature for 15 minutes. The cell membrane permeation treatment was performed by passing 0.2% Triton-X100 (PBS (−) solution), filling the vicinity of the filter therewith, and then causing reaction at room temperature for 15 minutes. The filter was washed with PBS (−), and liquid in the device was replaced. A flow channel that connected the supply port 41 and the separation portion was removed and was sealed with a cover glass, and then the number of SW620 cells that were captured by the filter was counted through microscopy.

After counting, the cover glass was removed, and an acrylic plate provided with wells for collection that was designed to correspond to the position and the size of the flow channel in the upper portion of the filter was set on the cover 48.

Thereafter, the cells that were captured by the filter were collected. 1 ml of PBS (−) (a collection liquid) was passed through the filter using the backflow liquid feeding mechanism in a direction (in the arrow B direction shown in FIG. 4) that was reverse of the liquid passing direction in which the above-described cells were captured (the flow rate was 6,000 ml/min). The collection liquid that stayed in the upper portion of the filter was suctioned with a pipette, and the total amount thereof was collected. The number of SW620 cells in the collected liquid was counted through microscopy. The collection ratio was obtained by dividing the number of SW620 cells in the collected liquid by the number of SW620 cells that were captured by the filter. The results are shown in Table 5 below.

Properties of Filter

Through hole short axial diameter: 6.5 μm, long axial diameter: 9.8 μm, area: 50 μm$^2$, shape: ellipse Pitch between centers of holes (short axial diameter side× long axial diameter side): 19 μm×14 μm
Hole density: 3,759 holes/mm$^2$
Opening ratio: 19%
Membrane thickness: 5 μm
Material: nickel
Filtering area: 20 mm$^2$ Experiment Example 12

Cells were captured and collected similarly to Experiment Example 11 except that the fixation treatment was performed through reaction with 1% PFA (PBS (−) solution) at room temperature for 10 minutes, and the cell membrane permeation treatment was performed by passing 0.2% Triton-X100 (PBS (−) solution) through the filter (a period of reaction time in a state in which the vicinity of the filter was filled with the solution was not provided, and reaction occurred only in the period of time while liquid was passed). The results are shown in Table 5 below.

Experiment Example 13

Cells were captured and collected similarly to Experiment Example 11 except that the fixation treatment was performed with 5 mg/ml dimethyl suberimidate:DMS (PBS (−) solution) at room temperature for 10 minutes, and the cell membrane permeation treatment was performed only by passing 0.2% Triton-X100 (PBS (−) solution). The results are shown in Table 5 below.

Experiment Example 14

First, cells were captured through filtering with a filter. With the same method as Experiment Example 1, 2 ml of a blood specimen containing unstained SW620 cells was passed at a constant pressure in the arrow A direction shown in FIG. 4 for approximately 8 minutes (ΔP1=0.4 kPa: filtering flow rate was 0.25 ml/min). Accordingly, SW620 cells was captured at the filter (the same filter as Experiment Example 1 except that the filtering area was 20 mm$^2$). Similarly to Experiment Example 1, the hemolysis treatment was performed, the sample was washed with PBS-EDTA, and then at the filter, the fixation treatment was performed with 1% PFA (PBS (−) solution) at room temperature for 10 minutes and the cell membrane permeation treatment was performed by passing 0.2% Triton-X100 (PBS (−) solution). Thereafter, FcR blocking treatment was performed and cells were stained with a fluorescently labeled anti-cytokeratin antibody. The cells were washed with PBS-EDTA, and liquid in the device was replaced. A flow channel that connected the supply port 41 and the separation portion was removed and was sealed with a cover glass, and then the number of SW620 cells that were captured by the filter was counted through microscopy.

After counting, the cover glass was removed, and an acrylic plate provided with wells for collection that was designed to correspond to the position and the size of the flow channel in the upper portion of the filter was set on the cover 48.

Thereafter, the cells that were captured by the filter were collected. 1 ml of PBS-EDTA (a collection liquid) was passed through the filter using the backflow liquid feeding mechanism in a direction (in the arrow B direction shown in FIG. 4) that was reverse of the liquid passing direction in which the above-described cells were captured (the flow rate was 6,000 ml/min). The collection liquid that stayed in the upper portion of the filter was suctioned with a pipette, and the total amount thereof was collected. The number of SW620 cells in the collected liquid was counted through microscopy. The collection ratio was obtained by dividing the number of SW620 cells in the collected liquid by the number of SW620 cells that were captured by the filter.

The results are shown in Table 5 below.

Experiment Example 15

First, cells were captured through filtering with a filter. A resin member was used as the member that fixed the filter, 8 ml of a blood specimen containing SUN-1 cells stained with Celltracker green and SW620 stained with Celltracker orange was passed in the arrow A direction shown in FIG. 4 at a constant flow rate for approximately 32 minutes (the filtering flow rate was 0.25 ml/min). Accordingly, SNU-1 cells and SW620 cells were captured on the filter (the same filter as Experiment Example 1). Next, after the cells were washed with the filter using 2 mL of PBS-EDTA four times, 900 μL of ACS was passed through the filter three times so as to cause hemolysis at room temperature similarly to Experiment Example 1 (in order to increase the accuracy of the counting after collection). The cells were washed using 2 mL of PBS-BSA four times, and liquid in the device was replaced.

Next, the cells that were captured by the filter were collected. 1 ml of PBS-BSA (a collection liquid, viscosity: 1.50 mPa·s) was passed using the backflow liquid feeding mechanism in a direction (in the arrow B direction shown in FIG. 4) that was reverse of the liquid passing direction in which the above-described cells were captured (the flow rate was 600 ml/min). Thereafter, after the collection liquid in the upper portion of the filter was stirred with a pipette two times, 500 μl of the collection liquid that stayed in the upper portion of the filter was collected through suction with a pipette, then stirred two times, and the remaining total amount was collected similarly. The number of SNU-1s and the number of SW620 cells in the collected liquid were counted through microscopy. The cell collection ratios were obtained by dividing the number of collected cells by the number of cells that were added. The results are shown in Table 5 below.

Experiment Example 16

Cells were captured and collected similarly to Experiment Example 15 except that the flow rate of the collection liquid was 316 ml/min (pressure of a passing liquid was 58 kPa). The results are shown in Table 5 below.

Experiment Example 17

Cells were captured and collected similarly to Experiment Example 15 except that the filtering area was 28 mm$^2$, the filtering flow rate was 0.1 ml/min, and NCI-H1650 (human lung cancer) cells that were stained with Celltracker green were used. The results are shown in Table 5 below.

Experiment Example 18

First, cells were captured through filtering with a filter. A resin member was used as the member that fixed the filter, 8 ml of a blood specimen containing unstained NCI-H1650 cells was passed in the arrow A direction shown in FIG. 4 at a constant flow rate for approximately 80 minutes (the filtering flow rate was 0.1 ml/min). Accordingly, NCI- H1650 cells were captured on the filter (the same filter as Experiment Example 1 except that the filtering area was 28 mm$^2$). Next, hemolysis treatment, fixation/cell membrane permeation treatment, cell staining such as antibody staining were performed on the captured NCI-H1650 cells, and lastly, liquid in the device was replaced through washing with an isotonic solution that was based on sucrose/glucose.

Next, the cells that were captured by the filter were collected. 1 ml of the above-described isotonic solution (a collection liquid, viscosity: 1.75 mPa·s) was passed using the backflow liquid feeding mechanism in a direction (in the arrow B direction shown in FIG. 4) that was reverse of the liquid passing direction in which the above-described cells were captured (the flow rate was 600 ml/min). Thereafter, after the collection liquid in the upper portion of the filter was stirred with a pipette two times, 250 μl of the collection liquid that stayed on the filter was collected, then stirred two times, and the remaining total amount was collected similarly. The number of NCI-H1650 cells in the collected liquid was counted through microscopy. The cell collection ratios were obtained by dividing the number of collected cells by the number of cells that were added. The results are shown in Table 5 below.

Experiment Example 19

Cells were captured and collected similarly to Experiment Example 18 except that the amount of the collection liquid was 0.5 ml. The results are shown in Table 5 below.

Experiment Example 20

Cells were captured and collected similarly to Experiment Example 18 except that the amount of the collection liquid was 0.5 ml and the filtering flow rate was 1 ml/min. The results are shown in Table 5 below.

Experiment Example 21

Cells were captured and collected similarly to Experiment Example 15 except that the filtering area was 28 mm$^2$, the filtering flow rate was 1 ml/min, the amount of the collection liquid was 0.5 ml, and the flow rate was 100 ml/min, and NCI-H1975 (human lung cancer) cells that were stained with Celltracker green were used. The results are shown in Table 5 below.

Experiment Example 22

Cells were captured and collected similarly to Experiment Example 21 except that SW620 cells that were stained with Celltracker orange were used. The results are shown in Table 5 below.

Experiment Example 23

Cells were captured and collected similarly to Experiment Example 21 except that NCI-H1650 cells that were stained with Celltracker green were used. The results are shown in Table 5 below.

Experiment Example 24

Cells were captured and collected similarly to Experiment Example 21 except that NCI-H1650 cells that were stained with Celltracker green were used and fixation treatment was added after hemolysis. The results are shown in Table 5 below.

Experiment Example 25

Cells were captured and collected similarly to Experiment Example 21 except that the flow rate of the collection liquid was 50 ml/min. The results are shown in Table 5 below.

Experiment Example 26

Cells were captured and collected similarly to Experiment Example 22 except that the flow rate of the collection liquid was 50 ml/min. The results are shown in Table 5 below.

Experiment Example 27

Cells were captured and collected similarly to Experiment Example 23 except that the flow rate of the collection liquid was 50 ml/min. The results are shown in Table 5 below.

Experiment Example 28

Cells were captured and collected similarly to Experiment Example 21 except that the flow rate of the collection liquid was 25 ml/min. The results are shown in Table 5 below.

Experiment Example 29

Cells were captured and collected similarly to Experiment Example 22 except that the flow rate of the collection liquid was 25 ml/min. The results are shown in Table 5 below.

Experiment Example 30

Cells were captured and collected similarly to Experiment Example 23 except that the flow rate of the collection liquid was 25 ml/min. The results are shown in Table 5 below.

Experiment Example 31

Cells were captured and collected similarly to Experiment Example 24 except that the flow rate of the collection liquid was 25 ml/min. The results are shown in Table 5 below.

Comparative Experiment Example 1

Cells were captured and collected similarly to Experiment Example 21 except that the flow rate of the collection liquid was 10 ml/min and SNU-1 cells that were stained with Celltracker green were used. The results are shown in Table 5 below.

Comparative Experiment Example 2

Cells were captured and collected similarly to Comparative Experiment Example 1 except that the flow rate of the collection liquid was 5 ml/min. The results are shown in Table 5 below.

Comparative Experiment Example 3

Cells were captured and collected similarly to Comparative Experiment Example 1 except that the flow rate of the collection liquid was 2.5 ml/min. The results are shown in Table 5 below.

Comparative Experiment Example 4

Cells were captured and collected similarly to Comparative Experiment Example 1 except that the flow rate of the collection liquid was 1 ml/min. The results are shown in Table 5 below.

Comparative Experiment Example 5

Cells were captured and collected similarly to Comparative Experiment Example 3 except that SW620 cells that were stained with Celltracker orange were used. The results are shown in Table 5 below.

TABLE 5

| | | Filtering (capture) conditions | | | | Collection conditions | | Flow rate ratio [collection flow rate/specimen flow rate] |
|---|---|---|---|---|---|---|---|---|
| | | liquid amount [mL] | passing time [min] | flow velocity per opening area [mm/sec] | liquid feeding method | collection liquid amount [mL] | flow velocity per opening area [mm/sec] | |
| Experiment Ex. | 1 | 7.5 | 30 | 0.13 | constant pressure | 1 | 62 | 480 |
| | 2 | 7.5 | 30 | 0.13 | constant pressure | 0.25 | 3,087 | 24,000 |
| | 3 | 7.5 | 30 | 0.13 | constant pressure | 0.5 | 3,087 | 24,000 |
| | 4 | 7.5 | 30 | 0.13 | constant pressure | 1 | 3,087 | 24,000 |
| | 5 | 7.5 | 30 | 0.13 | constant pressure | 0.25 | 309 | 2,400 |
| | 6 | 7.5 | 30 | 0.13 | constant pressure | 1 | 309 | 2,400 |
| | 7 | 7.5 | 60-120 | 0.13-0.25 | constant pressure | 1 | 1,220 | 4,800-9,600 |
| | 8 | 7.5 | 60-120 | 0.13-0.25 | constant pressure | 1 | 244 | 4,800-9,600 |
| | 9 | 4 | 30 | 0.26 | constant pressure | 1 | 244 | 923 |
| | 10 | 4 | 10 | 0.81 | constant pressure | 1 | 244 | 300 |
| | 11 | 2 | 8 | 1.10 | constant pressure | 1 | 26,316 | 24,000 |
| | 12 | 2 | 8 | 1.10 | constant pressure | 1 | 26,316 | 24,000 |
| | 13 | 2 | 8 | 1.10 | constant pressure | 1 | 26,316 | 24,000 |
| | 14 | 2 | 8 | 1.10 | constant pressure | 1 | 26,316 | 24,000 |
| | 15 | 8 | 32 | 0.13 | constant flow rate | 1 | 309 | 2,400 |
| | 16 | 8 | 32 | 0.13 | constant flow rate | 1 | 163 | 1,264 |
| | 17 | 8 | 32 | 0.15 | constant flow rate | 1 | 871 | 6,000 |
| | 18 | 8 | 80 | 0.15 | constant flow rate | 1 | 871 | 6,000 |
| | 19 | 8 | 80 | 0.15 | constant flow rate | 0.5 | 871 | 6,000 |
| | 20 | 8 | 8 | 1.45 | constant flow rate | 0.5 | 871 | 600 |
| | 21 | 8 | 8 | 1.45 | constant flow rate | 0.5 | 145 | 100 |
| | 22 | 8 | 8 | 1.45 | constant flow rate | 0.5 | 145 | 100 |
| | 23 | 8 | 8 | 1.45 | constant flow rate | 0.5 | 145 | 100 |
| | 24 | 8 | 8 | 1.45 | constant flow rate | 0.5 | 145 | 100 |
| | 25 | 8 | 8 | 1.45 | constant flow rate | 0.5 | 73 | 50 |
| | 26 | 8 | 8 | 1.45 | constant flow rate | 0.5 | 73 | 50 |
| | 27 | 8 | 8 | 1.45 | constant flow rate | 0.5 | 73 | 50 |
| | 28 | 8 | 8 | 1.45 | constant flow rate | 0.5 | 36 | 25 |
| | 29 | 8 | 8 | 1.45 | constant flow rate | 0.5 | 36 | 25 |
| | 30 | 8 | 8 | 1.45 | constant flow rate | 0.5 | 36 | 25 |
| | 31 | 8 | 8 | 1.45 | constant flow rate | 0.5 | 36 | 25 |
| Comp. Experiment Ex. | 1 | 8 | 8 | 1.45 | constant flow rate | 0.5 | 14.5 | 10 |
| | 2 | 8 | 8 | 1.45 | constant flow rate | 0.5 | 7.3 | 5.0 |
| | 3 | 8 | 8 | 1.45 | constant flow rate | 0.5 | 3.6 | 2.5 |
| | 4 | 8 | 8 | 1.45 | constant flow rate | 0.5 | 1.5 | 1 |
| | 5 | 8 | 8 | 1.45 | constant flow rate | 0.5 | 1.5 | 1 |

| | | Filter | | | | Fixation/ permeation treatment | Collection ratio |
|---|---|---|---|---|---|---|---|
| | | Filtering area [mm²] | Opening ratio | shape of hole | Cell | | |
| Experiment Ex. | 1 | 79 | 41% | slit | SUN-1 | no | 70% |
| | 2 | 79 | 41% | slit | SUN-1 | no | 98% |
| | 3 | 79 | 41% | slit | SUN-1 | no | 92% |
| | 4 | 79 | 41% | slit | SUN-1 | no | 86% |
| | 5 | 79 | 41% | slit | SUN-1 | no | 81% |
| | 6 | 79 | 41% | slit | SUN-1 | no | 87% |
| | 7 | 20 | 41% | slit | SUN-1 | no | 93% |
| | 8 | 20 | 41% | slit | SUN-1 | no | 91% |
| | 9 | 20 | 41% | slit | SUN-1 | no | 75% |
| | 10 | 20 | 41% | slit | SUN-1 | no | 79% |
| | 11 | 20 | 19% | ellipse | SW620 | yes | 73% |
| | 12 | 20 | 19% | ellipse | SW620 | yes | 76% |
| | 13 | 20 | 19% | ellipse | SW620 | yes | 75% |
| | 14 | 20 | 19% | ellipse | SW620 | yes + antibody staining | 74% |
| | 15 | 79 | 41% | slit | SUN-1 SW620 | no | 90% 99% |
| | 16 | 79 | 41% | slit | SUN-1 SW620 | no | 85% 90% |
| | 17 | 28 | 41% | slit | NCl-H1 650 | no | 111% |

TABLE 5-continued

| | | | | | | | | |
|---|---|---|---|---|---|---|---|---|
| | | 18 | 28 | 41% | slit | NCl-H1 650 | yes + antibody staining | 81% |
| | | 19 | 28 | 41% | slit | NCl-H1 650 | yes + antibody staining | 76% |
| | | 20 | 28 | 41% | slit | NCl-H1 650 | yes + antibody staining | 76% |
| | | 21 | 28 | 41% | slit | NCl-H1 975 | no | 85% |
| | | 22 | 28 | 41% | slit | SW620 | no | 98% |
| | | 23 | 28 | 41% | slit | NCl-H1 650 | no | 101% |
| | | 24 | 28 | 41% | slit | NCl-H1 650 | only fixation | 93% |
| | | 25 | 28 | 41% | slit | NCl-H1 975 | no | 79% |
| | | 26 | 28 | 41% | slit | SW620 | no | 105% |
| | | 27 | 28 | 41% | slit | NCl-H1 650 | no | 89% |
| | | 28 | 28 | 41% | slit | NCl-H1 975 | no | 80% |
| | | 29 | 28 | 41% | slit | SW620 | no | 85% |
| | | 30 | 28 | 41% | slit | NCl-H1 650 | no | 90% |
| | | 31 | 28 | 41% | slit | NCl-H1 650 | only fixation | 82% |
| Comp. Experiment Ex. | | 1 | 28 | 41% | slit | SNU-1 | no | 60% |
| | | 2 | 28 | 41% | slit | SNU-1 | no | 45% |
| | | 3 | 28 | 41% | slit | SNU-1 | no | 51% |
| | | 4 | 28 | 41% | slit | NCl-H1 650 | no | 49% |
| | | 5 | 28 | 41% | slit | SW620 | no | 64% |

As shown in Table 5, cells were collected from the filter at a collection ratio exceeding 70% in all of the examples. Also, a high collection ratio was realized with a small amount of the collection liquid.

Although in Experiment Examples 1 to 30 above, after the collection liquid was passed using the backflow liquid feeding mechanism, the total amount of the collection liquid that stayed in the upper portion of the filter was collected, there were cases where the collection ratio was further increased by collecting the collection liquid such that a small amount of the collection liquid remained on the filter, then, passing the collection liquid using the backflow liquid feeding mechanism again.

As shown in Table 5, the cells were collected from the filter at a high collection ratio exceeding 70% by setting the flow velocity of the collection liquid (per opening area) to at least 15 mm/sec or more, or 36 mm/sec or more.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for labeling particles with magnetic beads, the method comprising:
   supplying and feeding a specimen including the particles to a filter, the particles captured on a capture surface of the filter;
   filling with liquid a flow channel on the other surface of the filter, the other surface being opposite to the capture surface,
   supplying a suspension comprising magnetic beads onto the capture surface of the filter so as to create a state in which both the capture surface and the other surface of the filter are in contact with the suspension containing the magnetic beads;
   from the state in which both the capture surface and the other surface of the filter are in contact with the suspension containing the magnetic beads, reversely feeding the suspension comprising the magnetic beads through the filter from the other surface of the filter toward the capture surface of the filter; and
   passing the suspension comprising unreacted magnetic beads through the filter from the capture surface of the filter toward the other surface of the filter so that the unreacted magnetic beads are removed and the particles labeled with the magnetic beads are captured on the capture surface of the filter.

2. The method according to claim 1, comprising:
   stirring the suspension comprising the magnetic beads on the capture surface of the filter, after the reversely feeding.

3. The method according to claim 1, comprising:
   passing a collection liquid through the filter in a direction that is reverse of a direction in which the specimen comprising the particles passed through the filter to capture the particles, after the reversely feeding, and
   collecting the collection liquid staying on the filter through suction.

4. The method according to claim 1, comprising:
   capturing the particles with the filter by passing the specimen comprising the particles through the filter at a certain flow velocity.

5. The method according to claim 4, comprising:
   passing a collection liquid through the filter in a direction that is reverse of a direction in which the specimen comprising the particles passed through the filter, after the reversely feeding, and
   collecting the collection liquid staying on the filter through suction.

6. The method according to claim 4,
wherein the flow velocity of the specimen is 0.01 mm/sec to 100 mm/sec per opening area of the filter.

7. The method according to claim 4,
wherein a flow velocity at which the suspension is fed reversely is faster than 1/10 the flow velocity of the specimen.

8. The method according to claim 4,
wherein a flow velocity at which the suspension is fed reversely is 0.1 mm/sec or more per opening area of the filter.

9. The method according to claim 4,
wherein a flow velocity at which the suspension is fed reversely is faster than 1/5 the flow velocity of the specimen.

10. The method according to claim 4,
wherein a flow velocity at which the suspension is fed reversely is faster than 1/2 the flow velocity of the specimen.

11. The method according to claim 1,
wherein the flow velocity at which the suspension is fed reversely is 0.01 mm/sec or more per opening area of the filter.

12. The method according to claim 1,
wherein the particles are human or animal cells.

13. The method according to claim 1, wherein
the magnetic beads comprise one or more of avidin, streptavidin, neutravidin, an antibody, or an antigen.

\* \* \* \* \*